(12) United States Patent
Chu et al.

(10) Patent No.: US 8,841,440 B2
(45) Date of Patent: Sep. 23, 2014

(54) ORGANO-SOLUBLE CHITOSAN SALTS AND CHITOSAN-DERIVED BIOMATERIALS PREPARED THEREOF

(75) Inventors: Chih-Chang Chu, Ithaca, NY (US); Chao Zhong, Seattle, WA (US)

(73) Assignee: Cornell University, Ithaca, NY (US)

( * ) Notice: Subject to any disclaimer, the term of this patent is extended or adjusted under 35 U.S.C. 154(b) by 591 days.

(21) Appl. No.: 12/935,660

(22) PCT Filed: Apr. 1, 2009

(86) PCT No.: PCT/US2009/002017
§ 371 (c)(1),
(2), (4) Date: Jan. 25, 2011

(87) PCT Pub. No.: WO2009/123713
PCT Pub. Date: Oct. 8, 2009

(65) Prior Publication Data
US 2011/0150999 A1   Jun. 23, 2011

Related U.S. Application Data

(60) Provisional application No. 61/064,887, filed on Apr. 1, 2008.

(51) Int. Cl.
*C07B 37/08* (2006.01)
*C08B 37/08* (2006.01)

(52) U.S. Cl.
CPC ................................... *C08B 37/003* (2013.01)
USPC ........................................................ 536/55.1

(58) Field of Classification Search
None
See application file for complete search history.

(56) References Cited

U.S. PATENT DOCUMENTS

| | | | |
|---|---|---|---|
| 3,879,376 A * | 4/1975 | Vanlerberghe et al. | ......... 536/20 |
| 4,929,722 A | 5/1990 | Partain, III et al. | |
| 5,061,792 A | 10/1991 | Albisetti et al. | |
| 5,599,916 A * | 2/1997 | Dutkiewicz et al. | ............ 536/20 |
| 5,821,221 A | 10/1998 | Shalaby et al. | |
| 6,130,321 A | 10/2000 | Johnson et al. | |
| 2003/0206958 A1 | 11/2003 | Cattaneo et al. | |
| 2007/0281904 A1 | 12/2007 | Baker et al. | |
| 2009/0035356 A1 | 2/2009 | Bui-Khac et al. | |

FOREIGN PATENT DOCUMENTS

| | | | |
|---|---|---|---|
| GB | 771138 A | | 3/1957 |
| WO | 2007/028244 A1 | | 3/2007 |
| WO | WO2008/081257 | * | 10/2008 |
| WO | 2008/141452 A1 | | 11/2008 |

OTHER PUBLICATIONS

Sashiwa, et al., Dissolution of Chitosan in Dimethyl Sulfoxide by Salt Formation, The Chemical Society of Japan [online], 2000, vol. 29, No. 6, pp. 596-597.

* cited by examiner

*Primary Examiner* — Eric S Olson
(74) *Attorney, Agent, or Firm* — Hodgson Russ LLP

(57) ABSTRACT

Organo-soluble chitosan salts, method for preparing organo-soluble salts, chitosan-derived materials prepared with organo-soluble chitosan salts, and methods for preparing chitosan-derived materials are disclosed.

5 Claims, 12 Drawing Sheets

Cytotoxicity of N,O-maleic Chitosan
A10: Smooth Muscle cell
NRK49: Fibroblast Cell
4H,48H means incubation time in cell media for 4 hours and 48 hours, respectively.

Cytotoxicity of Maleic Chitosan-PEGDA Hydrogel
(A10: Smooth Muscle cell)

Cytotoxicity of Maleic Chitosan-PEGDA Hydrogel
(Rat Smooth Muscle Primary Cell)
48 Hours FTIR
a) Chitosan
b) b) poly-benzyl-glutamate-Chitosan Hybrid
c) polyglutamic acid-chitosan (water soluble)

1HNMR( Chitosan/ poly (Z-benzyl-glutamic acid)

1HNMR Chitosan/ poly-(glutamic acid)

ORGANO-SOLUBLE CHITOSAN SALTS AND CHITOSAN-DERIVED BIOMATERIALS PREPARED THEREOF

CROSS-REFERENCE TO RELATED APPLICATIONS

This application is a national phase of PCT/US2009/002017 filed on Apr. 1, 2009, which claims priority to U.S. Provisional Application No. 61/064,887 filed on Apr. 1, 2008.

FIELD OF INVENTION

The present invention relates to organo-soluble chitosan salts, a method for preparing organo-soluble salts, chitosan derivatives prepared from organo-soluble chitosan salts, and a method for preparing the chitosan derivatives.

BACKGROUND OF THE INVENTION

Chitosan, as a biocompatible and biodegradable polysaccharide, has attracted considerable attention from various industries. VandeVord, P. J., Matthew, H. W. T., DeSilva, S. P., Mayton, L., Wu, B., Wooley, P. H.; *J. Biomed. Mater. Res.* 2002, 59, 585-590. Many attempts have been made to modify the molecular structure of chitosan in order to introduce certain properties into the molecule. Yu et al., *Biomacromolecules;* 8(5); 1425-1435 (2007).

However, chemical reactions with chitosan are usually carried out under harsh and heterogeneous conditions (i.e., higher temperature and longer reaction time compared with the corresponding homogeneous conditions) and often involve multi-step protection and deprotection protocols due to the poor solubility of the molecule in common organic solvents. A typical approach is to 1) react chitosan directly with a cyclic anhydride in a solution such as dimethylformamide and water at a temperature of 100° C.-120° C. to obtain a first intermediate; 2) react the first intermediate with a pyridine and reactant such as triphenylchloromethane at 85° C.-105° C. to obtain a second intermediate; and 3) react the second intermediate with further reactants such as hydrazine monohydrate and water at a temperature of 100° C.-120° C. to obtain a final product. The reaction is exemplified as follows:

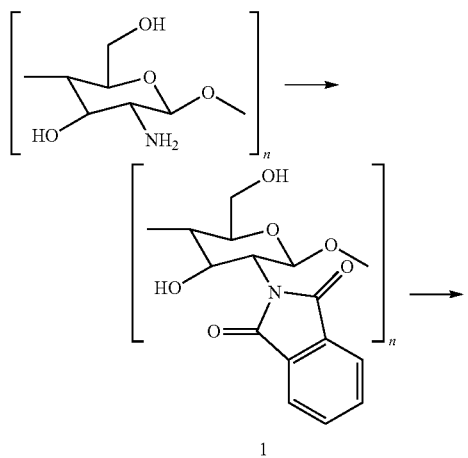

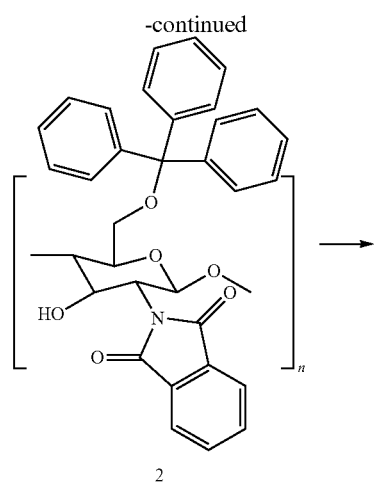

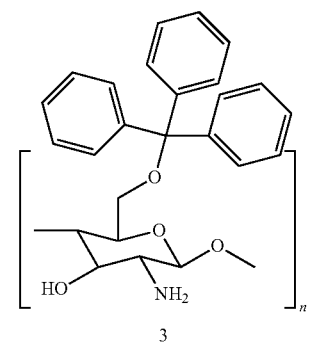

However, the final products resulting from these type of reactions have a number of drawbacks Holappa et al., *Macromolecules,* 37, 2784-2789 (2004). For example, the final products exhibit a low degree of substitution (low modification level due to low reaction activity) and/or an uncontrollable (random) substitution of the functional groups present in chitosan.

The inventors of the present application have discovered an efficient manner for producing organo-rouble chitosan salt under mild conditions. The organo-soluble chitosan salt in turn can be used to produce a novel chitosan derivative.

SUMMARY OF THE INVENTION

The first embodiment of the invention relates to a method for making an organo-soluble chitosan salt, comprising dispersing chitosan in an aqueous solution to form a mixture, adding a chitosan salt forming acid to the mixture, stirring the mixture containing the chitosan salt forming acid to form a homogenous solution, adding a solvent to the homogenous solution to precipitate an organo-soluble chitosan salt, and recovering the organo-soluble chitosan salt.

In a second embodiment, an organo-soluble chitosan salt, which is soluble in an organo-soluble chitosan salt solubility test, is disclosed that is soluble in dimethyl sulfoxide and formamide, as measured by a solubility test carried out with 10 mg salt samples dissolved in 1 ml of DMSO or formamide.

A third embodiment relates to a method for preparing chitosan derivative, comprising obtaining an organo-soluble chitosan salt, dissolving the organo-soluble chitosan salt in a first solvent to form a mixture, adding a chitosan derivative forming compound to the mixture, reacting the chitosan derivative forming compound with the organo-soluble chitosan salt to obtain a reaction solution containing the chitosan derivative, stopping the reaction, adding a second solvent to the reaction solution to precipitate the chitosan derivative, and recovering the chitosan derivative.

A fourth embodiment of the invention relates to a method for preparing a chitosan derivative, comprising dispersing chitosan in a first solvent to form a mixture; adding a chitosan salt forming acid to the mixture; adding chitosan derivative forming compound to the mixture; reacting the chitosan derivative forming compound, chitosan, and chitosan salt forming acid to obtain a reaction solution containing a chitosan derivative; stopping the reaction; adding a second solvent to the reaction solution to precipitate the chitosan derivative; and recovering the chitosan derivative.

A fifth embodiment of the invention relates to a chitosan derivative.

A sixth embodiment relates to compositions containing the chitosan derivative

The term "chitosan" means herein a group of polymers of acetylglucosamine, but with a degree of deactylation.

The phrase "chitosan salt forming acid" means herein any acid that can be used to form a chitosan salt in accordance with the present invention. In particular, chitosan salt forming acids that can be used in accordance with the present invention produced organo-soluble chitosan salts having an improved solubility in organic solvents.

An "organo-soluble chitosan salt solubility test" mean herein a test, wherein 10 mg of organo-soluble chitosan salt sample is dispersed in both 1 ml of 100% DMSO and 100% formamide. The mixture is set aside for 24 hours and then studied to determine whether the organo-soluble chitosan salts are soluble (i.e., completely dissolved), partially soluble (i.e., partially soluble), or undissolved.

The phrase "chitosan derivative forming compound" means herein any compound that can be used to form a chitosan salt in accordance with the present invention.

The term "hydrogel" is used herein to mean a polymeric material which exhibits the ability to swell in water and to retain a significant portion of water within its structure without dissolving.

The term "photocrosslinking" is used herein to mean causing vinyl bonds to break and form crosslinks by the application of radiant energy.

DETAILED DESCRIPTION OF THE INVENTION

Figure 1:
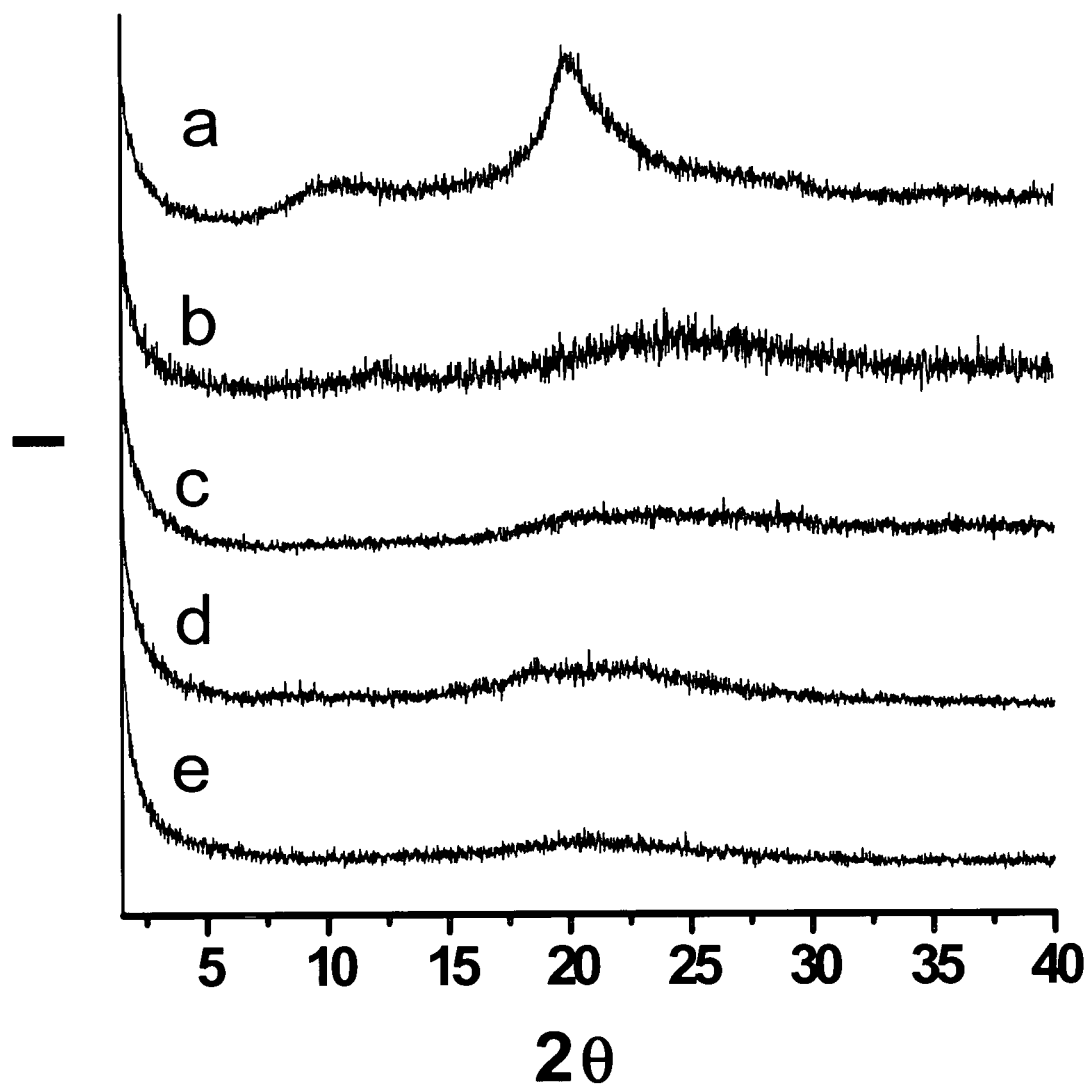
FIG. 1 shows an X-ray diffraction diagram of (a) chitosan, (b) hydrochloride acid chitosan salt, c) acetic acid chitosan salt, (d) methanesulfonic chitosan salt and (e) tolunesulfonic chitosan salt.

The first embodiment of the invention relates to a method for making an organo-soluble chitosan salt, comprising dispersing chitosan in an aqueous solution to form a mixture, adding a chitosan salt forming acid to the mixture, stirring the mixture containing the chitosan salt forming acid to form a homogenous solution, adding a solvent to the homogenous solution to precipitate an organo-soluble chitosan salt, and recovering the organo-soluble chitosan salt.

Chitosan and chitosan salts generally have a wide range of molecular weights. Chitosan and chitosan salts having a relatively high molecular weight are preferred for use in the present invention. Nonetheless, chitosan having a wide range of molecular weights can be used in accordance with the present invention.

Since chitosan is generally insoluble in water at 25° C., it is common to indirectly measure the viscosity of the chitosan by measuring the viscosity of a corresponding chitosan salt, such as by using a 1 weight percent acetic acid aqueous solution. Chitosan or chitosan salts suitable for use in the present invention will preferably have a viscosity in a 1.0 weight percent aqueous solution at 25° C. of from about 100 centipoise (100 mPa·s) to about 80,000 centipoise (80,000 mPa·s), more preferably from about 500 centipoise (500 mPa·s) to about 60,000 centipoise (60,000 mPa·s), and most preferably from about 1,000 centipoise (1,000 mPa·s) to about 50,000 centipoise (50,000 mPa·s).

Chitosan is produced commercially by deacetylation of chitin. The degree of acetylation refers to the average number of acetyl groups present on the anhydroglucose unit of the chitosan material. The degree of deacetylation can be determined by NMR spectroscopy. Chitosan having a varying degree of acetylation can be used in accordance with the present invention can vary. In one aspect, the chitosan has a degree of acetylation of 60-99%.

Chitosan is generally known to be a crystalline material. The degree of crystallinity generally depends on the source of the chitosan and its processing history. In this regard, the chitosan is preferably in powder or crystalline form.

The chitosan is initially dispersed into an aqueous solution to form a chitosan-containing mixture. The aqueous solution is preferably water, and more preferably deionized water. The large number of free amine groups present in chitosan makes chitosan a polymeric weak base. Chitosan is insoluble in water, dilute aqueous bases, and most organic solvents. Chitosan is soluble in dilute aqueous acids, usually carboxylic acids, as a chitosonium salt.

In this regard, a chitosan salt forming acid is also added to the mixture. The chitosan salt forming acid can be any acid that allows the formation of an organo-soluble chitosan salt that is soluble in organic solvents. A preferred feature of the invention is that is the organo-soluble salt is soluble in both DMSO and formamide, as measured by an organo-soluble chitosan salt solubility test.

In one fact of this embodiment, the chitosan salt forming acid is selected from the group consisting of formic acid, acetic acid, sulfonic acid (e.g., alkyl or allyl sulfonic acid), methanesulfonic acid, p-toluenesulfonic acid, camphorsulfonic acid, salicylic acid, trifluoromethanesulfonic acid, and mixtures thereof. A preferred aspect is that the chitosan salt forming acid is methanesulfonic acid, or p-toluenesulfonic acid.

In yet another facet of this embodiment, the chitosan salt forming acid is a short chain sulfonic acid. These short chain sulfonic acids are preferably characterized as having functional groups distinct from that mainly exhibited by chitosan (e.g., mainly hydroxyl —OH and amine —NH$_2$) or other functional groups (e.g., thiol —SH) that can react with chitosan. In a preferred aspect, the chitosan derivative formed with short chain sulfonic acid characterized as follows:

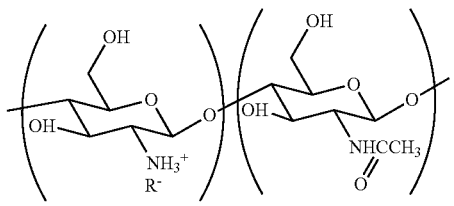

wherein R— is selected from the group consisting of ethanesulfonic acid (CH$_3$CH$_2$SO$_3$H)

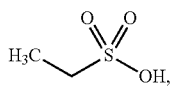

1-propanesulfonic acid (CH$_3$CH$_2$CH$_2$SO$_3$H)

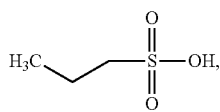

phenylbenzimidazolesulfonic acid (C$_{13}$H$_{10}$N$_2$O$_3$S)

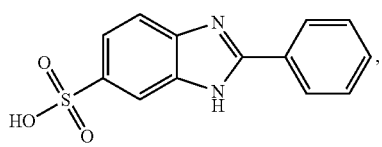 [SMILES: O=S(=O)(O)c1ccc2nc(-c3ccccc3)[nH]c2c1]

(1R)-(−)-10-camphorsulfonic acid (C$_{10}$H$_{16}$O$_4$S)

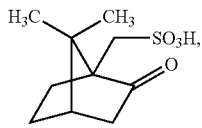

camphorquinone-10-sulfonic acid (C$_{10}$H$_{14}$O$_5$S)

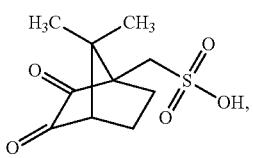 [SMILES: CC1(C)C2CCC1(CS(=O)(=O)O)C(=O)C2=O]

2-(trimethylsilyl)ethanesulfonic acid ((CH$_3$)$_3$SiCH$_2$CH$_2$SO$_3$H)

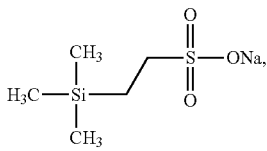

and trifluoromethanesulfonic acid (CF$_3$SO$_3$H)

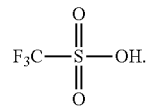

A sufficient amount of chitosan salt forming acid is added so that the chitosan salt forming acid can react with chitosan. The chitosan salt forming acid is preferably added to the mixture in an equimolar amount relative to the amount of chitosan.

In order to facilitate the dissolution of chitosan, the solution can be stirred with a stirring bar for 1-6 hours, preferably 1-2 hours. The solution thus obtained becomes a relatively transparent and homogeneous solution.

The temperature at which the reaction occurs can vary. However, the reaction preferably occurs at a temperature of 15° C. to 35° C., and more preferably occurs at room temperature (i.e., 20° C. to 25° C.). In yet another feature of this embodiment, the temperature never exceeds 75° C., preferably never exceeds 90° C., and more preferably never exceeds 100° C. It is also a preferred feature of this embodiment that protection reactions, deprotection reactions and harsh acid treatment conditions are excluded.

The reaction can be exemplified as follows:

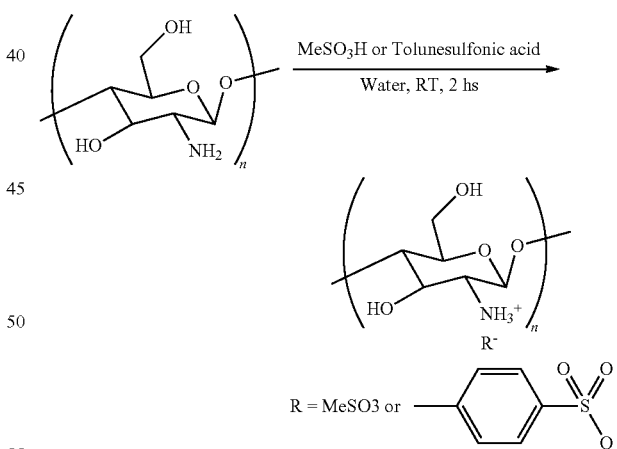

A solvent is added to the solution to precipitate an organo-soluble chitosan salt. The solvent is preferably acetone or an alcohol such as isopropanol. A preferred feature is that the organo-soluble chitosan salt is precipitated prior to any additional steps, such as dialyzing and/or drying the organo-soluble chitosan salt.

The precipitated organo-soluble chitosan salt can be optionally washed with additional solvents such as acetone. Once washed, the organo-soluble chitosan salts is recovered optionally by filtration. The filtration step can be completed with variety of filtration techniques and devices.

The organo-soluble chitosan salts can then be dried with a drying process such as vacuum filtration or freeze-drying. A preferred aspect of this embodiment is that the organo-soluble chitosan salts are precipitated with a solvent prior to being dried. The yield of product (i.e., an organo-soluble chitosan salt) varies form 60-99%, and preferably 89% to 99%.

The purity of the organo-soluble chitosan salts is optionally improved in yet another step by redissolving the organo-soluble chitosan salt in an aqueous solution, and then dialyzing the organo-soluble chitosan salt against the aqueous solution using a dialysis membrane. The dialysis membrane has a molecular weight cut-off of 20,000 D, preferably 10,000 D, more preferably 5,000 D, and even more preferably 3,500 D.

The final product is a purified organo-soluble chitosan salt.

We turn now to the second embodiment.

The organo-soluble chitosan salts of the second embodiment are soluble in organic solvents. In one aspect, the organo-soluble chitosan salts are soluble and/or partially soluble in DMSO and formamide, as measured by an organo-soluble chitosan salt solubility test.

In one facet of this embodiment, the organo-soluble chitosan salts are selected from the group consisting of chitosan sulfonate, chitosan methanesulfonate, chitosan toluenesulfonate, chitosan camphorsulfonate, chitosan salicylate, and chitosan trifluoromethanesulfonate. The organo-soluble chitosan salts are preferably chitosan methanesulfonate and chitosan toluenesulfonate. Examples of chitosan methanesulfonate and chitosan toluene sulfonate salts are as follows:

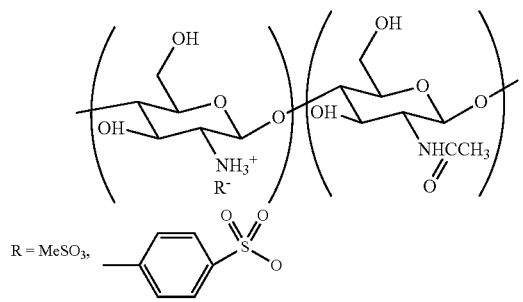

In yet another facet, the organo-soluble chitosan salts are selected from the group consisting of chitosan ethanesulfonate, chitosan phenylbenzimidazolesulfonate, chitosan 1-propanesulfonate, (1R)-(−)-10-camphorsulfonate, and chitosan camphorquinone-10-sulfonate.

In a preferred embodiment, the organo-soluble salts of this embodiment are obtained with the method described in the first embodiment. It is believed that the mild conditions utilized in the method of the first embodiment produces an organo-soluble chitosan salt having little to no polymer backbone degradation as compared to organo-soluble chitosan salts obtained with conventional methods, i.e., methods that utilize harsh and heterogeneous reaction conditions.

The milder conditions in which the organo-soluble chitosan salts of the present invention are believed to produce an organo-soluble chitosan salt and chitosan derivatives produced with the organo-soluble salts having improved properties. For example, chitosan derivatives produced with the organo-soluble salts of the present invention are substituted with functional groups. In a preferred feature of the invention, chitosan derivatives produced with the organo-soluble exhibits a higher degree of substitution as compared to chitosan organo-soluble chitosan salts obtained with under harsh and heterogeneous reaction conditions. In addition, the position and degree of substitution of the chitosan derivatives of the present invention can also be controlled.

We turn now to the third embodiment, which relates to a method for preparing a chitosan derivative, comprising obtaining an organo-soluble chitosan salt, dissolving the organo-soluble chitosan salts in a first solvent to form a mixture, adding a chitosan derivative forming compound to the mixture, reacting the chitosan derivative forming compound with the organo-soluble chitosan salts to obtain a reaction solution containing a chitosan derivative, stopping the reaction, adding a second solvent to the reaction solution to precipitate the chitosan derivative, and recovering the chitosan derivative.

An organo-soluble chitosan salt in accordance with the first and/or second embodiment is dispersed in an organic solvent, such as formamide, DMSO or a mixture thereof. The organo-soluble chitosan salt is added in amount of 1-25% by weight, and preferably 1-5% by weight of the resulting solution. A preferred feature of this embodiment is that the organo-soluble chitosan salt is added to the solution while the solution is being stirred. The organo-soluble chitosan salts typically dissolves within 30 minutes-5 hours, 30 minutes-2 hours and more preferably 1-2 hours. This step preferably occurs at temperature of 15° C. to 35° C., and more preferably occurs at room temperature (i.e., 20° C. to 25° C.).

A chitosan derivative forming compound can then be added to the solution. The chitosan derivative forming compound is a compound that be can reacted with an organo-soluble chitosan salt in accordance with the embodiments of this invention to provide a chitosan derivative soluble in organic solvents. The chitosan derivative can also have a functional double bond (we should describe this double bond further) and carboxyl functional groups. The chitosan derivatives are preferably water soluble, biocompatible, negatively charged and biodegradable. A preferred feature of the invention the substitution of the C2, C3 and/or C6 positions can be controlled. The positions are exemplified as follows:

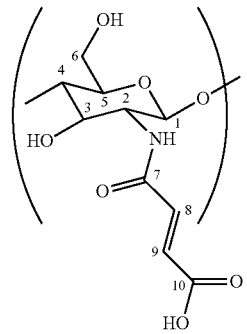

A preferred feature is a chitosan derivative, wherein the chitosan derivative forming compound is a cyclic anhydride, preferably a cyclic anhydride having the carbon-carbon double bond in the ring (e.g., maleic anhydride). As to maleic anhydride, the ring in maleic anhydride is subject to a ring opening mechanism. The acid of the maleic anhydride resulting form the ring opening attaches to amine groups of the C2 carbon of the chitosan as shown above. The carbon-carbon double bond that was present in the ring is now incorporated into the chitosan derivative ending with a carboxyl group, which itself can be functionalized with other compounds or form gels via photo-means.

In yet another feature, N-carboxy α-amino acid anhydrides (NCA) can be reacted with the chitosan salts. A ring opening reaction is utilized to prepare a chitosan derivative. Although NCAs are anhydrides, NCAs are different from cyclic anhydride as the NCA reaction results in a reaction that similar to a living polymerization. As result, a long polypeptide chain can be attached to chitosan after the reaction.

A first step in preparing a chitosan derivative, wherein NCA is the chitosan forming derivative is preparing an amino acid-NCA agent (AA2NCA). An alpha-amino acid, protected or not protected, is reacted a temperate of 20° C.-75° C., preferably 40° C.-50° C. with a reactant such as triphosgene for 1-6 hours, preferably 2-4 hours. The reaction results in an amino acid NCA. An example of the reaction is as follows:

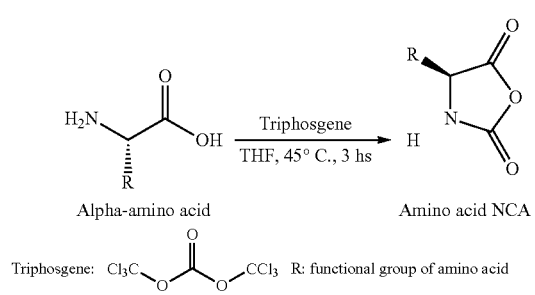

Examples of amino acids than can be used in the reaction are as follows:

| Name | Side Chain R |
| --- | --- |
| glycine | H— |
| alanine | CH$_2$— |
| valine | (CH$_3$)$_2$CH— |
| leucine | (CH$_3$)$_2$CHCH$_2$— |
| phenylalanine | (benzyl)CH$_2$— |
| protected aspartic acid | (benzyl ester) |
| protected glutamic acid | (benzyl ester) |
| protected lysine | (Cbz-protected) |

In a next step, the AA2NCA is grafted to the chitosan salt. The chitosan salt is dispersed in an organic solvent, preferably DMSO or formamide and at temperate of 20° C. to 35° C., preferably at room temperature to obtain chitosan derivative polypeptide. The chitosan salt used in the reaction is preferably a chitosan salt of the second embodiment. An reaction with methanesulfonate or toluenesuflonate is exemplified as follows:

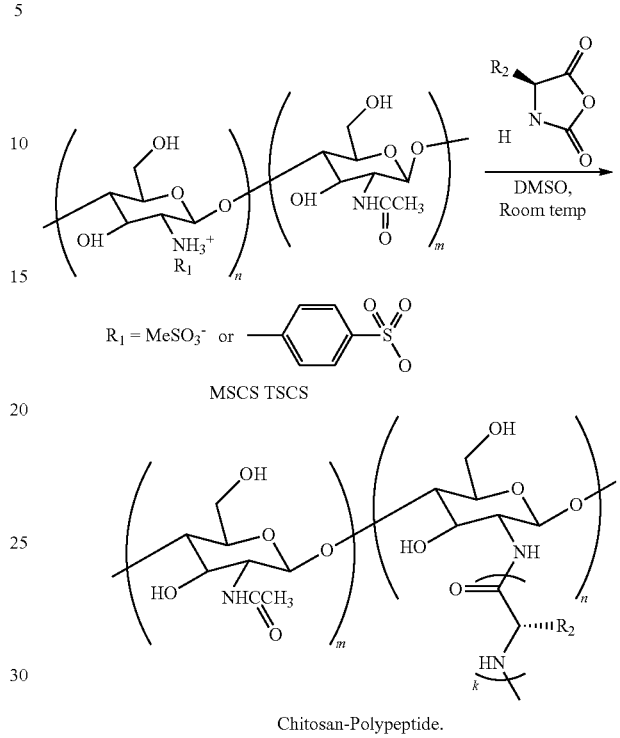

Chitosan-Polypeptide.

R$_2$ Depends on the amino acid used

In facets where the alpha-amino acid is protected, a reaction remixing the protecting groups can be utilized to restore original functional groups in amino acids.

An example is as follows:

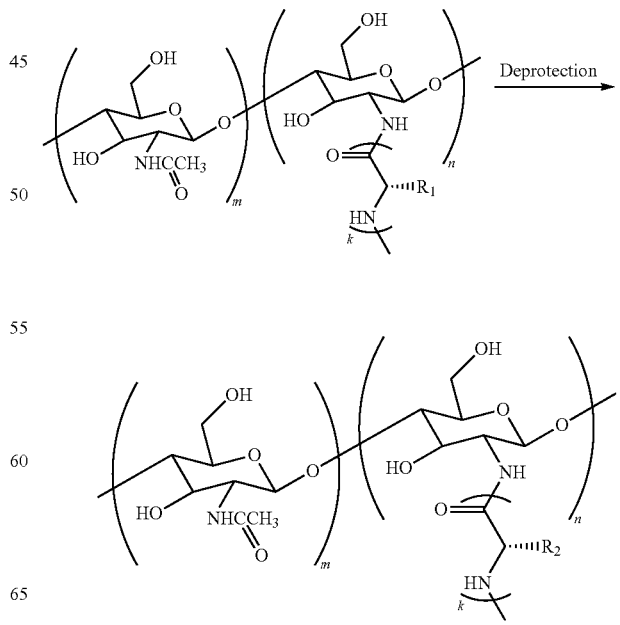

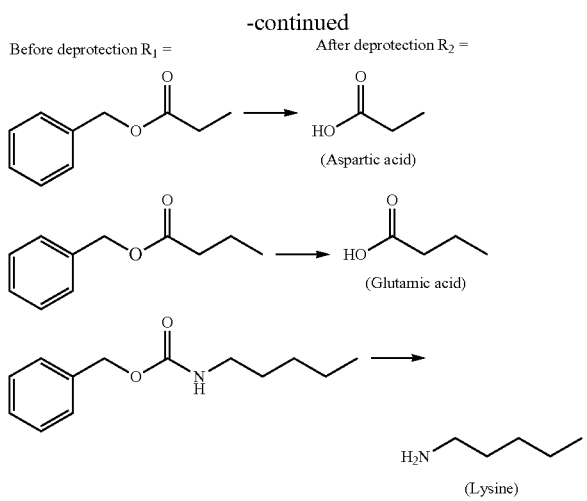

The chitosan derivative forming compound is preferably added in a 2-10 fold molar ratio of sugar units, and more preferably 4.5 to 6.5 fold molar ratio of sugar units. The reaction of the chitosan derivative forming compound with organo-soluble salt is preferably carried under stirring and with the protection of a gas such as N2 at a temperature of 30-90° C., preferably 40-75° C., and more preferably 50-70° C. for 6 to 72 hrs and preferably 12 to 36 hours. A preferred feature of the invention is that an acid is not added during the reaction and/or the temperature never exceeds 90° C., and preferably never exceeds 100° C.

Reaction with an organo-soluble chitosan salt and cyclic anhydride is exemplified as follows:

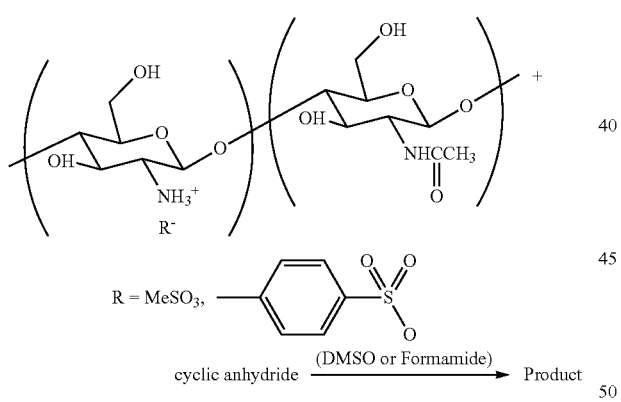

Once a sufficient amount of chitosan derivative is produced, the reaction is then stopped. A solvent such as acetone, an alcohol, or isopropanol can then be added to the mixture to precipitate out the chitosan derivative. In a preferred aspect of this embodiment, the precipitation step is carried out under stirring.

The precipitated chitosan derivative is optionally washed with yet another solvent such as acetone, an aqueous solution, or alcohol. Once washed, the chitosan derivative is recovered e.g., by filtration. The filtration step can be completed with variety of filtration techniques and devices.

The chitosan derivative can be dried with a drying process such as vacuum filtration or freeze-drying.

The chitosan derivative can be optionally further modified. For example, the chitosan derivative can be subject to hydrolysis. The hydrolysis allows for allow a wide range of regioselective N-acylation modifications of chitosan. For example, maleic chitosan can be further modified to obtain chitosan derivative compounds such as N-maleic chitosan, or N,O-maleic chitosan. The complete removal of ester groups on N, O-maleic chitosan by a hydrolysis strategy result in N-maleic chitosan. Hence, the simple synthetic route derived from the methanesulfonic (or tolunesulfonic) chitosan salt intermediates, coupled with a hydrolysis strategy in a strong basic solution, will allow a wide range of regioselective N-acylation modifications of chitosan.

N, O-maleic chitosan is produced redissolving the chitosan derivative in a solvent such as NaHCO$_3$ and in an amount to form a substantially transparent solution for 1-4 hours, and preferably 2 hours. The modified chitosan derivative in solution can then be dialyzed against and aqueous solution (e.g., deionized water) using a dialysis membrane. The dialysis membrane has a molecular weight cut-off of 20,000 D, preferably 10,000 D, more preferably 5,000 D, and even more preferably 3,500 D.

The modified chitosan derivative can then be recovered and dried. For example, the chitosan derivative can be freeze-dried with liquid nitrogen. The final yields of the product preferably range from 60%~95%.

The production of a modified maleic chitosan (i.e., N, O maleic chitosan is exemplified as follows:

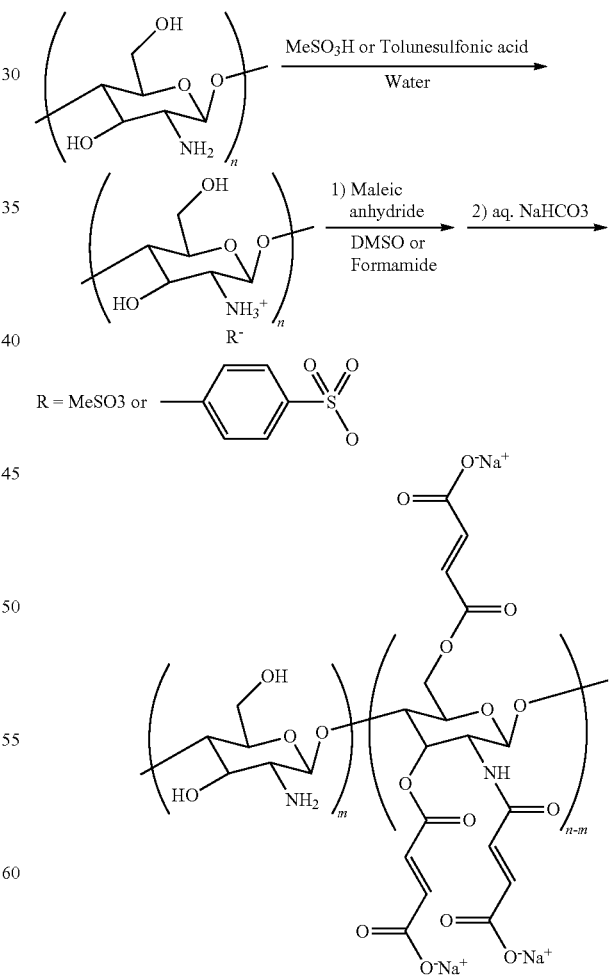

A fourth embodiment of the invention relates to a method for preparing a chitosan derivative, comprising dispersing chitosan in a first solvent to form a mixture; adding a chitosan salt forming acid to the mixture; adding chitosan derivative forming compound to the mixture; reacting the chitosan derivative forming compound, chitosan, and chitosan salt forming acid to obtain a reaction solution containing a chitosan derivative; stopping the reaction; adding a second solvent to the reaction solution to precipitate the chitosan derivative; and recovering a chitosan derivative.

A chitosan salt forming acid (e.g., as discussed in the first embodiment) and chitosan are directly dispersed together in an organic solvent such as formamide, DMSO, or mixtures. In other words, the organo-soluble chitosan salts of the first and second embodiments are not used directly. Rather, a sufficient amount of chitosan salt forming acid and chitosan salt can react. The chitosan salt forming acid is preferably added to the aqueous in an equimolar amount relative to the amount of chitosan.

In order to facilitate the dissolution of chitosan, the solution can be stirred with a stirring bar for 1-6 hours, preferably 1-2 hours. The solution thus obtained becomes a relatively transparent and homogeneous solution.

The temperature at which the reaction occurs can vary. However, the reaction preferably occurs at temperature of 15° C. to 35° C., and more preferably occurs at room temperature (i.e., 20° C. to 25° C.). In yet another preferred feature of this embodiment, the temperature never exceeds 75° C., preferably never exceeds 90° C., and more preferably never exceeds 100° C. It is also a preferred feature of this embodiment is that protection reactions, deprotection reactions and harsh acid treatment conditions are excluded.

A chitosan derivative forming compound (e.g., in accordance with the third embodiment) is then added to the solution and reacted with the chitosan and chitosan salt forming acid to produce a chitosan derivative. The chitosan derivative forming compound is preferably added in a 2-10 fold molar ratio of sugar units, and more preferably 4.5 to 6.5 fold molar ratio of sugar units. The reaction of the chitosan derivative forming compound with organo-soluble salt is preferably carried under stirring and with the protection of a gas such as N2 at a temperature of 30-90° C., preferably 40-75° C., and more preferably 50-70° C. for 6 to 72 hrs and preferably 12 to 36 hours. A preferred feature of the invention is that an acid is not added during the reaction and/or the temperature never exceeds 90° C., and preferably never exceeds 100° C.

Once the resulting chitosan derivative is produced, the chitosan derivative can be further processed in accordance with same steps, conditions and reactants as disclosed in the third embodiment. Similar products and yields are also obtained.

The fifth embodiment of the invention relates to a chitosan derivative.

In a preferred case, the chitosan derivative is produced in accordance with the third or fourth embodiments.

The chitosan derivative is water soluble, biocompatible, negatively charged and biodegradable. The chitosan derivative also has a functional double bond (we should describe this double bond further) and carboxyl functional groups. The chitosan derivatives are preferably water soluble, biocompatible, negatively charged and biodegradable. A preferred feature of the invention is that the chitosan derivative forming compound can attach to the organo-soluble chitosan salt at the C2, C3 and/or C6 positions.

The acid of the chitosan derivative forming compound can be from those chitosan derivative forming compounds discussed in the third and fourth embodiments. In a preferred embodiment, the chitosan derivative forming compound is maleic anhydride and the maleic anhydride is used to produce maleic chitosan.

An example of maleic chitosan in accordance with the present invention is as follows:

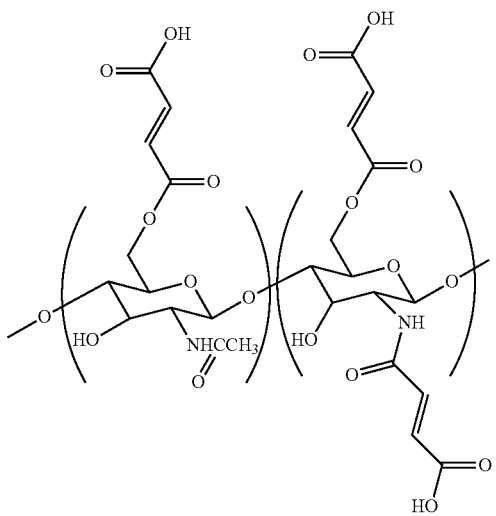

In a preferred feature, the chitosan derivative is substituted at the C2, C3 and/or C6 positions and the chitosan derivative has a degree of substitution of 0.55 to 1.75 and preferably a degree of substitution of 1.2-1.6.

The carboxyl functional group(s) on the chitosan derivative can be substituted with a bioactive material such as a positively charged amino acid, peptide, antibiotic, drug, polypeptide, anti-inflammatory agent, anti-platelet agent, anti-coagulation agent, immuno-suppressive agents, nitric oxide derivative, antimicrobial agents, growth factors, polymers, gel forming polymers, and combinations thereof. In one aspect of the invention, the chitosan derivative is substituted with PEGDA, TEMPO, or GRGD.

As used herein, an "amino acid" is a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acid (e.g. phosphoserine; phosphothreonine; phosphotyrosine; hydroxyproline; gamma-carboxyglutamate; hippuric acid; octahydroindole-2-carboxylic acid; statine; 1,2,3,4,-tetrahydroisoquinoline-3-carboxylic acid; penicillamine; omithine; citruline; α-methyl-alanine; para-benzoylphenylalanine; phenylglycine; propargylglycine; sarcosine; and tert-butylglycine) residue having one or more open valences. The term also comprises natural and unnatural amino acids bearing amino protecting groups (e.g. acetyl, acyl, trifluoroacetyl, or benzyloxycarbonyl), as well as natural and unnatural amino acids protected at carboxy with protecting groups (e.g. as a (C1-C6) alkyl phenyl or benzyl ester or amide). Other suitable amino and carboxy protecting groups are known to those skilled in the art (See for example, T. W. Greene, Protecting Groups In Organic Synthesis; Wiley: New York, 1981; D. Voet, Biochemistry Wiley: New York, 1990; L. Stryer, Biochemistry, (3rd Ed), W.H. Freeman and Co.: New York, 1975; J. March, Advanced Organic Chemistry, Reactions, Mechanisms and Structure, (2nd Ed.), McGraw Hill: New York, 1977; F. Carey and R. Sundberg, Advanced Organic Chemistry, Part B; Reactions and Synthesis, (2nd Ed.), Plenum: New York, 1977; and references cited therein). According to the invention, the amino or carboxy protecting group can also comprise a non-metallic radionuclide (e.g., Fluorine-18, Iodine-123, or Iodine-124).

The term "amino acid" includes alpha amino acids and beta amino acids. The alpha amino acids include monocarboxylic monoamino acids, dicarboxylic monoamino acids, polyamino acids and heterocyclic amino acids. Examples of monocarboxylic monoamino acids include glycine, alpha-phenylglycine, alpha-alanine, serine, valine, norvaline, beta-mercaptovaline, threonine, cysteine, leucine, isoleucine, norleucine, N-methylleucine, beta-hydroxy leucine, methionine, phenylalanine, N-methylphenylalanine, pipecolic acid, sarcosine, selenocysteine, tyrosine, 3,5-diiodotyrosine, triiodothyronine, and thyroxine. Examples of monoamino dicarboxylic acids and amides include aspartic acid, beta-methyl aspartic acid, glutamic acid, asparagine, alpha-aminoadipic acid, 4-keto-pipecolic acid, lanthionine, and glutamine. Examples of polyamino acids include omithine, lysine, 6-N-methyllysine, 5-hydroxylysine, desmosine, argmine and cystine. Examples of heterocyclic amino acids include proline, 4-hydroxyproline and histidine, and tryptophan. Examples of other alpha amino acids are gamma-carboxyglutamate and citrulline. The beta amino acids include, for example, beta-alanine.

As used herein, a "peptide" is a sequence of 2 to 25 amino acids (e.g. as defined hereinabove) or peptidic residues having one or more open valences. The sequence may be linear or cyclic. For example, a cyclic peptide can be prepared or may result from the formation of disulfide bridges between two cysteine residues in a sequence. A peptide can be linked through the carboxy terminus, the amino terminus, or through any other convenient point of attachment, such as, for example, through the sulfur of a cysteine. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right. A preferred peptide is GRGD.

Suitable antibiotics include Adriamycin PFS/RDF® (Pharmacia & Upjohn), Blenoxane® (Bristol-Myers Squibb Oncology/Immunology), Cerubidine® (Bedford), Cosmegen® (Merck), DaunoXome® (NeXstar), Doxil® (Sequus), Doxorubicin Hydrochloride® (Astra), Idamycin® PFS Pharmacia & Upjohn), Mithracin® (Bayer), Mitamycin® (Bristol-Myers Squibb Oncology/Immunology), Nipen® (SuperGen), Novantrone® (Immunex) and Rubex® (Bristol-Myers Squibb Oncology/Immunology). Suitable antimetabolites include Cytostar-U® (Pharmacia & Upjohn), Fludara® (Berlex), Sterile FUDR® (Roche Laboratories), Leustatin® (Ortho Biotech), Methotrexate® (Immunex), Parinethol® (Glaxo Wellcome), Thioguanine® (Glaxo Wellcome) and Xeloda® (Roche Laboratories).

One or more drugs can be linked directly or indirectly linked with a linker to the chitosan derivatives. Specifically, the drugs can each be directly linked to the carboxyl group of the chitosan derivatives. Any suitable number of drugs can be directly linked to the chitosan derivatives. A drug is a therapeutic agent or a diagnostic agent and includes any substance, other than food, used in the prevention, diagnosis, alleviation, treatment, or cure of a disease. Stedman's Medical Dictionary 25th Edition, Illustrated (1990) p. 486. The substance can be taken by mouth; injected into a muscle, the ski, a blood vessel, or a cavity of the body; or topically applied. Mosby's Medical, Nursing & Allied Health Dictionary, Fifth Edition, (1998) p. 516. The drug can include any substance disclosed in at least one of: The Merck Index, 12th Edition (1996); Concise Dictionary of Biomedicine and Molecular Biology. Pei-Show Juo, (1996); U.S. Pharmacopeia Dictionary 2000 Edition; and Physician's Desk Reference, 2001 Edition.

Specifically, the drug can include, but is not limited to, one or more: polypeptides, therapeutic antibodies abeiximab, anti-inflammatory agents, blood modifiers, anti-platelet agents, anti-coagulation agents, immune suppressive agents, anti-neoplastic agents, anticancer agents, anti-cell proliferation agents, and nitric oxide releasing agents.

Polypeptides can have any suitable length. Specifically, the polypeptides can be about 2 to about 5,000 amino acids in length, inclusive; about 2 to about 2,000 amino acids in length, inclusive; about 2 to about 1,000 amino acids in length, inclusive; or about 2 to about 100 amino acids in length, inclusive.

The polypeptides can also include "Peptide mimetics". Peptide analogs are commonly used in the pharmaceutical industry as non-peptide drugs with properties analogous to those of the template peptide. These types of non-peptide compound are termed "peptide mimetics" or "peptide mimetics". Fauchere, J. (1986) Adv. Drug Res. 15:29; Veber and Freidinger (1985) TINS p. 392; and Evans et al. (1987) J. Med. Chem., 30: 1229; and are usually developed with the aid of computerized molecular modeling. Generally, peptidomimetics are structurally similar to a paradigm polypeptide (i.e., a polypeptide that has a biochemical property or pharmacological activity), but have one or more peptide linkages optionally replaced by a linkage selected from the group consisting of: —CH2NH—, —CH2S—, CH2-CH2-, —CHH— (cis and trans), —COCH2-, —CH(OH)CH2-, and —CH2SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A F., Vega Data (March 1983), Vol. 1, Issue 3, "Peptide Backbone Modifications" (general review); Morley, J. S., Trends. Pharm. Sci., (1980) pp. 463-468 (general review); Hudson, D. et al., Int J. Pept. Prot. Res., (1979) 14:177-185 (—CH2NH—, CH2CH2-); Spatola, A. F. et al., Life Sci., (1986) 38:1243-1249 (—CH2-S—); Hann, M. M., J. Chem. Soc. Perkin Trans I (1982) 307-314 (—CH=CH—, cis and trans); Almquist, R. G. et al., J. Med. Chem., (1980) 23:1392-1398 (—COCH2-); Jennings-White, C. et al., Tetrahedron Lett., (1982) 23:2533 (—COCH2-) Szelke, M. et al., European Appin., EP 45665 (1982) CA: 97:39405 (1982) (—CH(OH)CH2-); Holladay, M. W. et al., Tetrahedron Lett., (1983) 24:4401-4404 (—C(OH)CH2-); and Hruby, V. J., Life Sci., (1982) 31:189-199 (—CH2-S—). Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Additionally, substitution of one or more amino acids within a polypeptide with a D-amino acid of the same type (e.g., D-lysine in place of L-lysine) can be used to generate more stable polypeptides and polypeptides resistant to endogenous proteases.

In one aspect, the polypeptide can be an antibody. Examples of such antibodies include single-chain antibodies, chimeric antibodies, monoclonal antibodies, polyclonal antibodies, antibody fragments, Fab fragments, IgA, IgG, IgM IgD, IgE and humanized antibodies. In one embodiment, the antibody can bind to a cell adhesion molecule, such as a cadherin, integrin or selectin. In another case, the antibody can bind to an molecule, such as collagen, elastin, fibronectin or laminin. In still another case, the antibody can bind to a receptor, such as an adrenergic receptor, B-cell receptor, complement receptor, cholinergic receptor, estrogen receptor, insulin receptor, low-density lipoprotein receptor, growth factor receptor or T-cell receptor. Antibodies of the invention can also bind to platelet aggregation factors (e.g., fibrinogen), cell proliferation factors (e.g., growth factors and cytokines), and blood clotting factors (e.g., fibrinogen).

In another case, an antibody can be conjugated to an active agent, such as a toxin. In another case, the antibody can be Abciximab (ReoPro(R)). Abeiximab is an Fab fragment of a chimeric antibody that binds to beta(3) integrins. Abciximab is specific for platelet glycoprotein IIb/IIIa receptors, e.g., on blood cells. Human aortic smooth muscle cells express alpha(v)beta(3) integrins on their surface. Treating beta(3) expressing smooth muscle cells may prohibit adhesion of other cells and decrease cellular migration or proliferation, thus reducing restinosis following percutaneous coronary interventions (CPI) e.g., stenosis, angioplasty, stenting. Abciximab also inhibits aggregation of blood platelets.

In one case, the peptide can be a glycopeptide. "Glycopeptide" refers to oligopeptide (e.g. heptapeptide) antibiotics, characterized by a multi-ring peptide core optionally substituted with saccharide groups, such as vancomycin. Examples of glycopeptides included in this definition may be found in "Glycopeptides Classification, Occurrence, and Discovery", by Raymond C. Rao and Louise W. Crandall, ("Drugs and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327; 5,591,714; 5,840,684; and 5,843,889; in EP 0 802 199; EP 0 801 075; EP 0 667 353; WO 97/28812; WO 97/38702; WO 98/52589; WO 98/52592; and in J. Amer. Chem. Soc., 1996, 118, 13107-13108; J. Amer. Chem. Soc., 1997, 119, 12041-12047; and J. Amer. Chem. Soc., 1994, 116, 4573-4590. Representative glycopeptides include those identified as A477, A35512, A40926, A41030, A42867, A47934, A80407, A82846, A83850 A84575, AB65, Actaplanin, Actinoidin, Ardacin, Avoparcin, Azureomycin, Balhimycin, Chloroorientiein, Chloropolysporin, Decaplanin, -demethylvancomycin, Bremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MMS6598, OA-7653, Orenticin, Parvodicin, Ristocetin, Ristomycin, Synmonicin, Teicoplanin, UK-68597, UK-69542, UK-72051, Vancomycin, and the like. The term "glycopeptide" or "glycopeptide antibiotic" as used herein is also intended to include the general class of glycopeptides disclosed above on which the sugar moiety is absent, i.e. the aglycone series of glycopeptides. For example, removal of the disaccharide moiety appended to the phenol on vancomycin by mild hydrolysis gives vancomycin aglycone. Also included within the scope of the term "glycopeptide antibiotics" are synthetic derivatives of the general class of glycopeptides disclosed above, included alkylated and acylated derivatives. Additionally, within the scope of this term are glycopeptides that have been further appended with additional saccharide residues, especially aminoglycosides, in a manner similar to vancosamine.

In one facet, the peptide can be lapidated glycopeptides. The term "lipidated glycopeptide" refers specifically to those glycopeptide antibiotics which have been-synthetically modified to contain a lipid substituent. As used herein, the term "lipid substituent" refers to any substituent contains 5 or more carbon atoms, preferably, 10 to 40 carbon atoms. The lipid substituent may optionally contain from 1 to 6 heteroatoms selected from halo, oxygen, nitrogen, sulfur and phosphorous. Lipidated glycopeptide antibiotics are well-known in the art See, for example, in U.S. Pat. Nos. 5,840,684, 5,843,889, 5,916,873, 5,919,756, 5,952,310, 5,977,062, 5,977,063, EP 667,353, WO 98/52589, WO 99/56760, WO 00/04044, WO 00/39156, the disclosures of which are incorporated herein by reference in their entirety.

Anti-inflammatory agents include, e.g., analgesics (e.g., NSAIDS and salicylates), antirheumatic agents, gastrointestinal agents, gout preparations, hormones (glucocorticoids), nasal preparations, ophthalmic preparations, otic preparations (e.g., antibiotic and steroid combinations), respiratory agents, and skin & mucous membrane agents. See, Physician's Desk Reference, 2001 Edition. Specifically, the anti-inflammatory agent can include dexamethasone, which is chemically designated as (11β, 16α)-9-fluoro-11,17,21-trihydroxy-16-methylpregna-1,4diene-3,20-dione. Alternatively, the anti-inflammatory agent can include sirolimus (rapamycin), which is a triene macrolide antibiotic isolated from *Streptomyces hygroscopicus*.

Anti-platelet and anticoagulation agents include, e.g., Coumadin® (DuPont), Fragmin® (Pharmacia & Upjohn), Heparin® (Wyeth-Ayerst), Lovenox®, Normiflo®, Organa® (Organon), Aggrastat® (Merck), Agrylin® (Roberts), Ecotrin® (Smithkline Beechamn), Flolan® (Glaxo Wellcome), Halfprin® (Kramer), Integrillin® (COR Therapeutics), Integrillin® (Key), Persantine® (Boehringer Ingelheim), Plavix® (Bristol-Myers Squibb), ReoPro® (Centecor), Ticlid® (Roche), Abbokinase® (Abbtt), Activase® (Genentech), Eminase® (Roberts), and Strepase® (Astra). See, Physician's Desk Reference, 2001 Edition. Specifically, the anti-platelet and anti-coagulation agent can include trapidil (avantrin), cilostazol, heparin, hirudin, or ilprost.

Trapidil is chemically designated as N,N-dimethyl-5-methyl-[1,2,4]triazolo[1,-5-a]pyrimidin4-amine. Cilostazol is chemically designated as 6-[4-(1-cyclohexyl-1H-tetrazol-5-yl)-butoxy]-3,4-dihydro-2(1H)-quinolinone.

Heparin is a glycosaminoglycan with anticoagulant activity; a heterogeneous mixture of variably sulfonated polysaccharide chains composed of repeating units of D-glucosamine and either L-iduronic or D-glucuronic acids. Hirudin is an anticoagulant protein extracted from leeches, e.g., Hirudo medicinalis. Iloprost is chemically designated as 5-[Hexahydro-5-hydroxy-4-(3-hydroxy-4-methyl-1-octen-6-ynyl)-2(1H)-pentalenylidene]pentanoic acid.

The immune suppressive agent can include, e.g., Azathioprine® (Roxane), BayRho-D® (Bayer Biological), CellCept® (Roche Laboratories), Imuran® (Glaxo Wellcome), MiCRhoGAM® (Ortho-Clinical Diagnostics), Neoran® (Novarts), Orthoclone OKT3® (Ortho Biotech), Prograf® (Fujisawa), PhoGAM® (Ortho-Clinical Diagnostics), Sandimmune® (Novartis), Simulect® (Novartis), and Zenapax® (Roche Laboratories). Specifically, the immune suppressive agent can include rapamycin or thalidomide. Rapamycin is a triene macrolide isolated from *Streptomyces hygroscopicus*. Thalidomide is chemically designated as 2-(2,6-dioxo-3-piperidinyl)-1H-iso-indole-1,3(2H)-dione.

In one case, a therapeutically effective amount of the nitric oxide (NO) derivative compound binds to the carboxylic acid of the chitosan derivative. Examples of such compounds are 2,2,5,5-tetramethylpyrrolidine-1-oxy; 2,2,5,5-tetramethyl-3-pyrroline-1-oxy-3-carbonyl; 4-(N,N-dimethyl-N-hexadecyl) ammonium-2,2,6,6-tetramethylpiperidine-1-oxy, iodide (CAT 16); 4-trimethylammonium-2,2,6,6-tetramethylpiperidine-1-oxy, iodide (CAT 1); 3-amino-2,2,5,5-tetramethylpyrrolidine-1-oxy; N-(3-(iodoacetyl)amino)-2,2,5,5-tetramethylpyrrolidine-1-oxy(PROXYL 1A); succinimidyl 2,2,5,5-tetramethyl-3-pyrroline-1-oxy-3-carboxylate; 2,2,5,5- tetramethyl-3-pyrroline-1-oxy-3-carboxylic acid; 2,2,6,6-tetramethylpiperidine-1-oxy; 4-amino-2,2,6,6-tetramethylpiperadine-1-oxy; 4-carboxy-2,2,6,6-tetramethylpiperadine-1-oxy; 4-acetamido-2,2,6,6-tetramethylpiperadine-1-oxy; 4-bromo-2,2,6,6-tetramethylpiperadine-1-oxy; 4-(N,N-dimethyl-N-(2-hydroxyethyl))ammonium-2,2,6,6-tetramethylpiperidine-1-oxy; 4-(N,N-dimethyl-N-(3-sulfopropyl)ammonium-2,2,6,6-tetramethylpiperidine-1-oxy; N-(4-(iodoacetyl)amino-2,2,6,6 tetramethylpiperidine-1-oxy; N-(2,2,6,6-tetramethylpiperidine-1-oxy-4-yl)maleimide; and mixtures thereof. A particularly preferred compound is 4-amino-2,2,6,6-tetramethylpiperadine-1-oxy radical.

A niticoxide like compound can also be produced. Suitable niticoxide like compounds are disclosed, e.g., in U.S. Pat. No. 5,650,447 and S-nitrosothiol derivative (adduct) of bovine or human serum albumin. See, e.g., Inhibition of neointimal proliferation in rabbits after vascular injury by a single treatment with a protein adduct of nitric oxide; David marks et al J. Clin. Invest. (1995); 96:2630-2638.

An antimicrobial is a substance that kills or inhibits the growth of microbes such as bacteria, fungi, protozoals or viruses. The antimicrobial can be anti-viral, anti-bacterial, anti-fungal agent, or metal (e.g., Ag, Cu, or Hg). In a preferred aspect, the antimicrobial is not attached to the chitosan derivative. Rather, the antimicrobial is immersed within and around the chitosan derivative. In yet another embodiment, silver is a preferred antimicrobial.

The term growth factor refers to a naturally occurring protein capable of stimulating cellular growth, proliferation and cellular differentiation. Growth factors are important for regulating a variety of cellular processes. Growth factors typically act as signaling molecules between cells. Examples are cytokines and hormones that bind to specific receptors on the surface of their target cells. They often promote cell differentiation and maturation, which varies between growth factors. For example, bone morphogenic proteins stimulate bone cell differentiation, while fibroblast growth factors and vascular endothelial growth factors stimulate blood vessel differentiation (angiogenesis). Examples of growth factors that can be used in accordance with the claimed invention include but are not limited to Endothelial growth factor (EGF), Erythropoietin (EPO), Fibroblast growth factor (FGF), Granulocyte-colony stimulating factor (G-CSF), Granulocyte-macrophage colony stimulating factor (GM-CSF), Growth differentiation factor-9 (GDF9), Hepatocyte growth factor (HGF), Insulin-like growth factor (IGF), Myostatin (GDF-8), Nerve growth factor (NGF), Platelet-derived growth factor (PDGF), Thrombopoietin (TPO), Transforming growth factor alpha(TGF-α), Transforming growth factor beta (TGF-β), Vascular endothelial growth factor (VEGF).

In a preferred aspect, a positively charged basic fibroblast growth factor (bFGF) is linked directly to a carboxyl group of the chitosan derivative.

In addition to being attached to or linked to one or more bioactive materials, either directly or through a linker, chitosan derivatives of the present invention can be physically intermixed with one or more bioactive materials to provide a chitosan-derived composition. As used herein, "intermixed" refers to a chitosan derivative of the present invention physically mixed with a bioactive material or a chitosan derivative of the present invention physically in contact with a bioactive material.

Any suitable amount of chitosan derivatives and bioactive material can be employed to provide a composition. The chitosan derivatives can be present in about 0.1 wt % to about 99.9 wt. % of the composition. Typically, the chitosan derivatives can be present above about 25 wt % of the composition; above about 50 wt % of the composition; above about 75 wt % of the composition; or above about 90 wt % of the composition.

In this regard, we turn now to the sixth embodiment, which relates to a composition containing the chitosan derivative.

The chitosan derivative can be used in a variety of applications, such to provide membranes, gels, hydrogels, blood coagulation products, wound healing products, bone regeneration materials, tissue engineering scaffolding, contact lenses, dental equipment, seed coatings, fertilizer, controlled agrochemical release compositions, dietary food additives, preservatives, antimicrobial textile finishes, wastewater treatment materials, cosmetics, lotions, moisturizers.

In one feature of this embodiment, the chitosan derivatives of the present invention are used to produce a hydrogel for a biological carrier. Chitosan derivatives are dissolved in an aqueous solution such as distilled water in appropriate weight ratios to give the concentrations denoted above, to make 10 to 30% (w/v) concentration solution. A photoinitiator is then added to the solution. Any photoinitiator can be used, but the photoinitiator is preferably 2,2-dimethoxy 2-phenyl acetophenone, 4-(2-hydroxyethoxy)phenyl-(2-hydroxy-2-propyl)ketone (Irgacure 2959) and DMPAP. The photoinitiator are preferably added in an amount of 0.01-10%, 0.1-3.0% (w/w). A solvent is optionally added depending on the type of photoinitiator used (e.g., DMPAP). The solvent, e.g., N-methylpyrrolidone, tetrahydrofuran, dimethyl formamide or dimethyl sulfoxide, is added to the solution. Photocrosslinking is carried out by UV irradiation, e.g., at room temperature, preferably 20° C. to 30° C., for 5 to 30 minutes, preferably 10 to 20 minutes. Unreacted chemicals are then preferably leached out of the resulting hydrogel. Drying of the hydrogel is preferably carried out by immersing in hot water (e.g., 35-75° C.) for 1-4 hours, preferably two hours to obtain shrinkage and drying of a shrunk hydrogel in a vacuum oven at 40-80° C., preferably 60° C. for 5 to 15 hours.

The hydrogels produced with the chitosan derivatives are useful for a variety of purposes including the controlled release of bioactive materials. In this aspect, the bioactive materials may be reacted with the free carboxyls in the chitosan derivatives to form covalent bonds between bioactive material and precursor or the bioactive material can be physically encapsulated or entrapped by the precursor. The bioactive material is released by metabolic action on the hydrogel, and the attachment to or entrapment in or encapsulation with hydrogel delays release, for example, for 2 to 48 hours or more.

The hydrogels from the chitosan derivatives herein are also useful as a temporary skin cover, e.g., as a wound dressing or artificial skin. In this case, the hydrogel can advantageously incorporate antimicrobial agent and/or would healing growth factor(s).

The hydrogels from the chitosan derivatives herein can also encapsulate viruses used in gene therapy to protect the viruses from the body's immune system until they reach the site where the genetic alteration is to occur. In conventional gene therapy, viruses are injected at the site of prospective incorporation and many injections are required to accommodate for inactivation of viruses. The hydrogels herein protect the viruses so that fewer injections may be utilized.

The hydrogels from the chitosan derivatives herein can also be useful for agricultural purposes to coat seeds. The hydrogel coating promotes retention of water during seed germination and promotes oxygen transport via pore structures and may include chemical agents, e.g., pesticides, for delivery to the seeds.

The hydrogels from the chitosan derivatives herein are useful for the administration of basic fibroblast growth factor (bFGF) to stimulate the proliferation of osteoblasts (i.e., promote bone formation) and to stimulate angiogenesis (development of blood vessels). The carboxylic acid groups in the chitosan derivatives serve as sites for the ionic bonding of bFGF. The hydrogels incorporating bFGF are applied to bone or blood vessels locally. Upon the biodegradation of the hydrogel, sustained release of bFGF for promoting bone growth and blood vessel formation is obtained. The bonding of the bFGF to the chitosan derivatives herein protects the bFGF against enzymatic degradation or denaturing so the bFGF can perform its biological functions and occurs because of the bFGF's inherent affinity toward acid compounds.

The hydrogels from the chitosan derivatives herein can be useful for integral components in microdevices, for example, biosensors. The carboxyl group in the hydrogel is very sensitive to various environmental stimuli, for example, pH and metal ions concentration, the swelling ratio and other properties of the hydrogel can accordingly change based on the change of controlled external stimuli.

The hydrogels from the chitosan derivatives herein are also useful in the cases where hydrogels are conventionally used, e.g., for thickening in foods, for moisture release to plants, for fluid uptake and retention in the sanitary area, as hydrophilic coatings for textile applications, for contact lenses and for separation and diffusion gel in chromatography and electrophoresis.

A biodegradable hydrogel herein is a hydrogel formed from a hydrogel forming system containing at least one biodegradable component, i.e., component which is degraded by water and/or by enzymes found in nature.

Bioactive molecules which are not reactive with components of the hydrogel-forming system herein can be physically entrapped within the hydrogel or physically encapsulated within the hydrogel by including them in the reaction mixture subjected to photocrosslinking so that the photocrosslinking causes formation of hydrogel with bioactive agent entrapped therein or encapsulated thereby.

In a preferred facet of this embodiment, a hydrogel is produced that can be used to form a scaffold for tissue engineering. For example, a GRGD group is attached onto a chitosan derivative through N-hydroxysuccinimide (NHS)— 1-Ethyl-3-[3-dimethylaminopropyl]carbodiimide hydrochloride (EDC) chemistry. The GRGD containing chitosan derivative can be photopolymerized into a functional hydrogel with good cell adhesive ability. The GRGD chitosan derivative gel can be used as a scaffold for tissue engineering scaffold (e.g., used as a template for further biomineralization to make bone tissue engineering scaffolds).

Furthermore, as noted above, an advantage of the chitosan derivatives of the present invention is that they can contain more than one free carboxyl groups. In this regard, the carboxyl group not containing a Gly-Arg-Gly-Asp (GRGD) group can be further biofunctionalized.

In a preferred aspect of this feature, the chitosan derivative is maleic chitosan and GRGD maleic chitosan is formed.

The reaction is exemplified as follows:

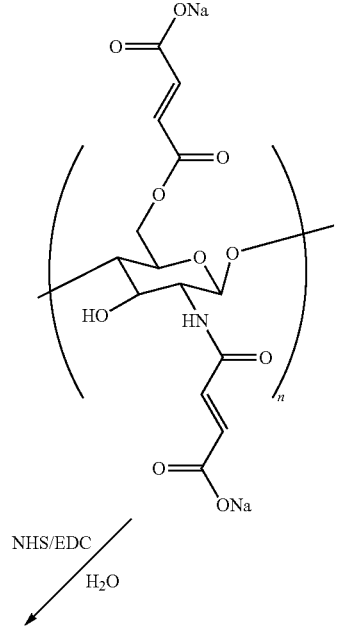

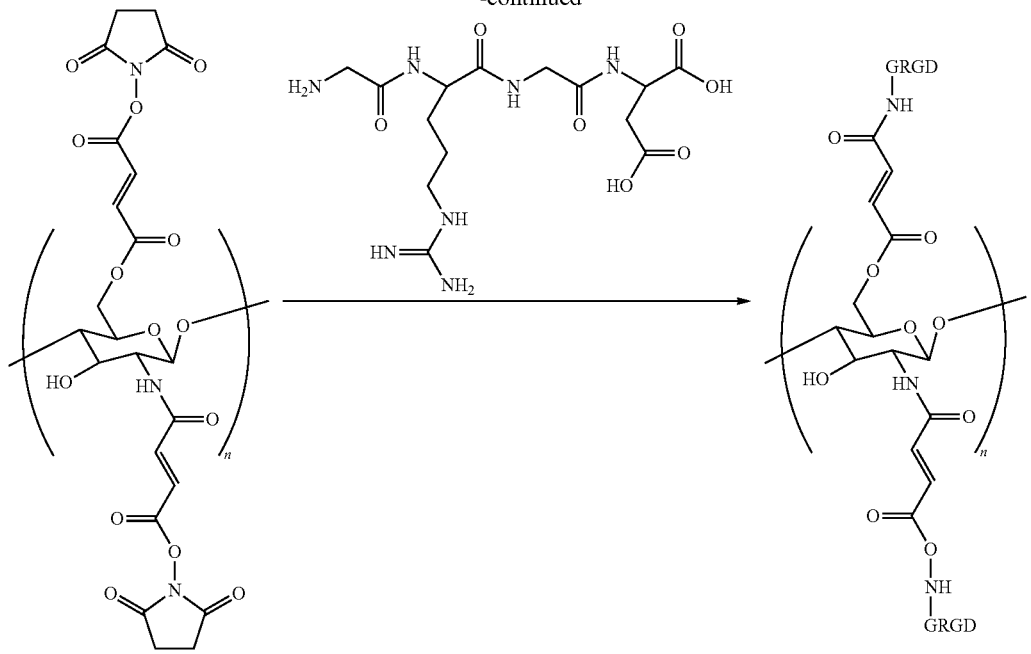

In one aspect, a chitosan derivative can be reacted with a polymer to form a gel. The gels themselves can be formed in an aqueous solution under UV light as discussed above. A chitosan derivative and biocompatible gel polymer such as PEGDA can be photopolymerized under ultraviolet light in an aqueous solution. A photoinitiator concentration can then be added in an amount of 0.01% to 10%, preferably 0.01% to 5% by weight of the solution. In forming the polymer-chitosan derivative based gel, the hydrogel strength and porosity can be controlled by adjusting the ratio between chitosan derivative and polymer, molecular weight of compounds, and degree of substitution of the chitosan derivative.

For example, this can be accomplished in a PEGDA-maleic chitosan compound by controlling the ratio between maleic chitosan and PEGDA, molecular weight of PEGDA, and degree of substitution of Maleic chitosan. In a preferred aspect, the gels are used as drug carriers, and tissue engineering scaffolds. In particular, as both PEGDA and Chitosan derivative are water soluble, this feature, coupled with consequent UV light-initiated photopolymerization, can therefore make this system as an injectable system for both drug delivery and tissue engineering application.

In a preferred feature of this embodiment, the chitosan derivative is maleic acid and the biocompatible polymer is PEGDA.

The structural formula is as follows:

The reaction itself can be exemplified as follows:

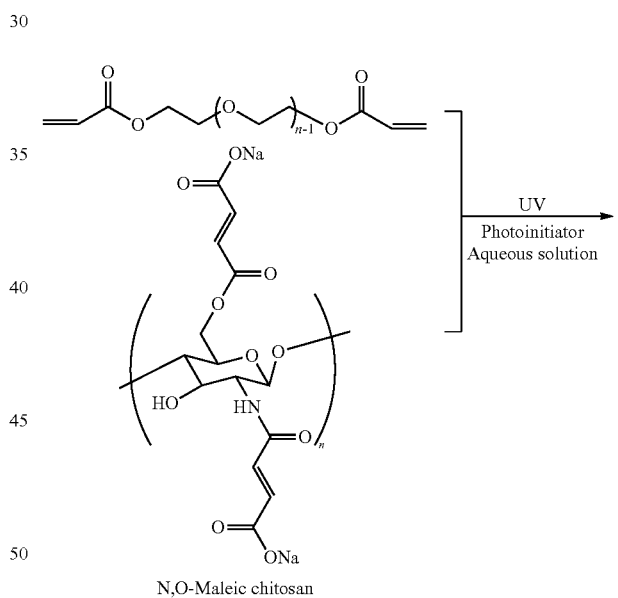

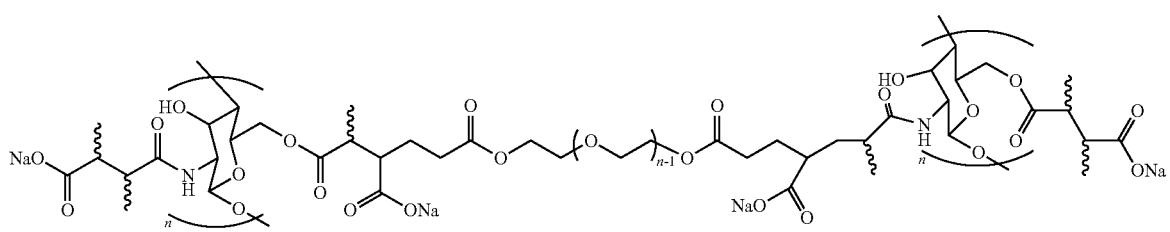

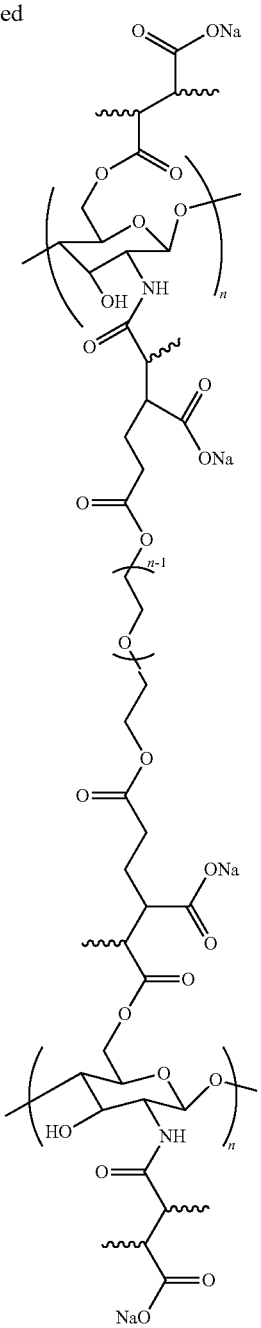

In yet another aspect, a PEGDA-maleic chitosan compound can be treated with antimicrobial as discussed in the fifth embodiment. In particular, the anionic carboxyl group in the maleic chitosan/PEGDA captures a silver ion from silver nitrate after maleic chitosan/PEGDA has been soaked in a aqueous solution containing silver nitrate.

The compositions can comprise, consist essentially of, or consist of the stated materials. The method can comprise, consist essentially of, or consist of the stated steps with the stated materials.

The foregoing description of the invention has been presented describing certain operable and preferred embodiments. It is not intended that the invention should be so limited since variations and modifications thereof will be obvious to those skilled in the art, all of which are within the spirit and scope of the invention.

Working examples for the invention are set forth below.

EXAMPLE 1

Synthesis of Chitosan Methanesulfonate 1.0 g of chitosan was dispersed in 100 ml deionized water. Methanesulfonic acid [molar ratio (acid: amine group)=1.2] was then added to the suspended solution and stirred for 2 hours. After 2 hours, chitosan was completely dissolved and was precipitated by addition of excess amounts of acetone or isopropanol. The precipitated product was washed with acetone for several times and dried in vacuum. The yields of the products ranged from 93~97%.

EXAMPLE 2

Synthesis of Maleic Chitosan

N, O-Maleic Chitosan 1.489 g methanesulfonic chitosan salts produced in EXAMPLE 1 were dissolved in 100 ml Formamide solvent under stirring at room temperature. 3.52 g of solid maleic anhydride 6-fold in molar ratio was then added to the solution. The reaction mixture was stirred under $N_2$ at 60° C. for 24 hrs.

The resulting product in the solution was precipitated out by acetone, filtered, washed with copious amounts of acetone, and dried. Methanesulfonic anions in the product were then removed from the chitosan salts by adding 0.1M $NaHCO_3$ solution. Finally the solution was dialyzed against deionized water for more than 3 days (MW cut off 12,000) and lyophilized to yield 89% of product.

EXAMPLE 3

N-Maleic Chitosan 0.5 g N, O-maleic chitosan was hydrolyzed in 20 ml 0.1M aqueous sodium hydroxide at room temperature for 10 h, and then dialyzed against deionized water for 3 days and lyophilized to give a product of 0.33 g.

EXAMPLE 4

Synthesis of Chitosan Tolunesulfonate 1.0 g of chitosan was dispersed in 100 mL deionized water. Tolunesulfonic acid [molar ratio (acid: amine group)=1.2] was then added to the suspended solution and stirred for 2 hours. After 2 hours, chitosan was completely dissolved and was precipitated by addition of copious amounts of acetone or isopropanol. The precipitated product was washed with acetone for several times and dried in vacuum. The yield of the product is 93%.

EXAMPLE 5

Synthesis of Maleic Chitosan Derivatives

N, O-Maleic Chitosan 1.875 g of tolunesulfonic chitosan salt obtained in EXAMPLE 4 is dissolved in 100 ml Formamide solvent under stirring at room temperature. 3.52 g of solid maleic anhydride of 6-fold in molar ratio was then added to form a solution, and the reaction mixture was stirred under $N_2$ at 60° C. for 24 hrs. The resulting product in the solution was precipitated out by acetone, filtered, washed with excess amounts of acetone, and dried. Tolunesulfonic anions in the product were then removed from the chitosan salts by adding 0.1M $NaHCO_3$ solution. Finally the solution was dialyzed against deionized water for more than 3 days (MW cut off 12,000) and lyophilized to yield 69%~89% of product.

EXAMPLE 6

N-Maleic Chitosan 0.5 g N, O-maleic chitosan obtained in EXAMPLE 5 was hydrolyzed in 20 ml 0.1M aqueous sodium hydroxide at room temperature for 10 h, and then dialyzed against deionized water for 3 days and lyophilized to give a N-maleic chitosan product of 0.33 g.

EXAMPLE 7

N, O-Maleic Chitosan Prepared From Chitosan Methanesulfonate and Chitosan Tolunesulfonate Methanesulfonic (MeSO3-) and toluenesulfonic (TSO3-) chitosan salts are used as intermediates for chemical synthesis of maleic chitosan either in formamide or DMSO. The use of chitosan methanesulfonate or toluenesulfonate as intermediates enabled the chemical reaction of chitosan with maleic anhydride in a homogeneous reaction mixture in organic solvents under a mild reaction condition. The degree of substitution (DS) and yield of the final maleic chitosan ranged from 0.58 to 1.53, and 69% to 89%, respectively, depending on the type of chitosan salt intermediates and solvents under optimum reaction conditions are shown as follows:

TABLE 1

| | Intermed. | Solvent | Solvents used for Precip. | DS | | | Total DS | Yield (%) |
| | | | | C-6 (O) | C-3 (O) | C-2 (N) | | |
|---|---|---|---|---|---|---|---|---|
| 1 | $MeSO_3^-$ CN | DMSO | Acetone | 0.24 | 0.03 | 0.32 | 0.58 | 69 |
| 2 | $TSO_3^-$ CN | DMSO | Isopropanol | 0.29 | 0.09 | 0.74 | 1.12 | 75 |
| 3 | $MeSO_3^-$ CN | Formamide | Acetone | 0.32 | 0.07 | 0.75 | 1.15 | 86 |
| 4 | $TSO_3^-$ CN | Formamide | Acetone | 0.64 | 0.10 | 0.80 | 1.53 | 89 |

EXAMPLE 8

Analysis of Product

Organo-soluble chitosan salts and N-maleic chitosan produced in accordance with the examples above and subject to x-ray diffraction and nuclear magnetic resonance.

As to the organo-soluble chitosan salts, the transformation of chitosan into chitosan salts is believed to have substantially destroyed the crystalline structure of chitosan, as confirmed by the XRD diagram shown in FIG. 1(a, d, e). In contrast to chitosan (FIG. 1a), both methanesulfonate and tolouenesulfonate chitosan salts almost exist in an amorphous state (FIGS. 1d & e), which explains their enhanced solubility in some organic solvents. However, their solubility in organic solvents also depends on the nature of counterion in salts. For example, the crystalline structure of the hydrochloride acid and acetic acid chitosan salts was completely destroyed (FIGS. 1b & c), these chitosan salts did not dissolve in any of the organic solvents tested other than water.

Figure 2A:
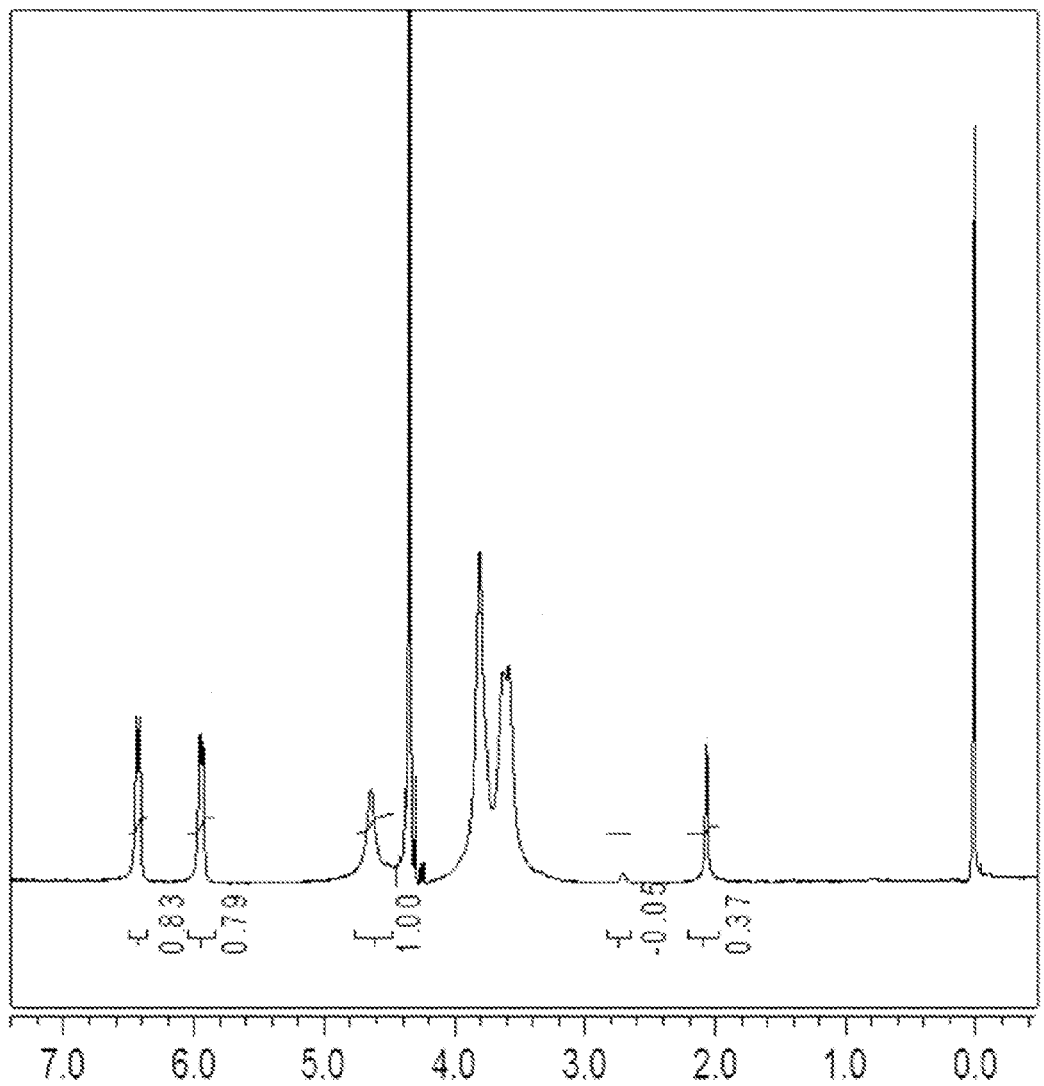
FIG. 2A-E show the results of (A) $^1$H NMR spectra of N-maleic chitosan, (B) $^{13}$C NMR spectra of N-maleic chitosan, (C) $^1$H NMR spectra of N, O-maleic chitosan, (D) $^1$H-$^1$H COSY of N, O-maleic chitosan (region of double bond signals), and (E) $^{13}$C NMR spectra of N, O-maleic chitosan.
Figure 2B:
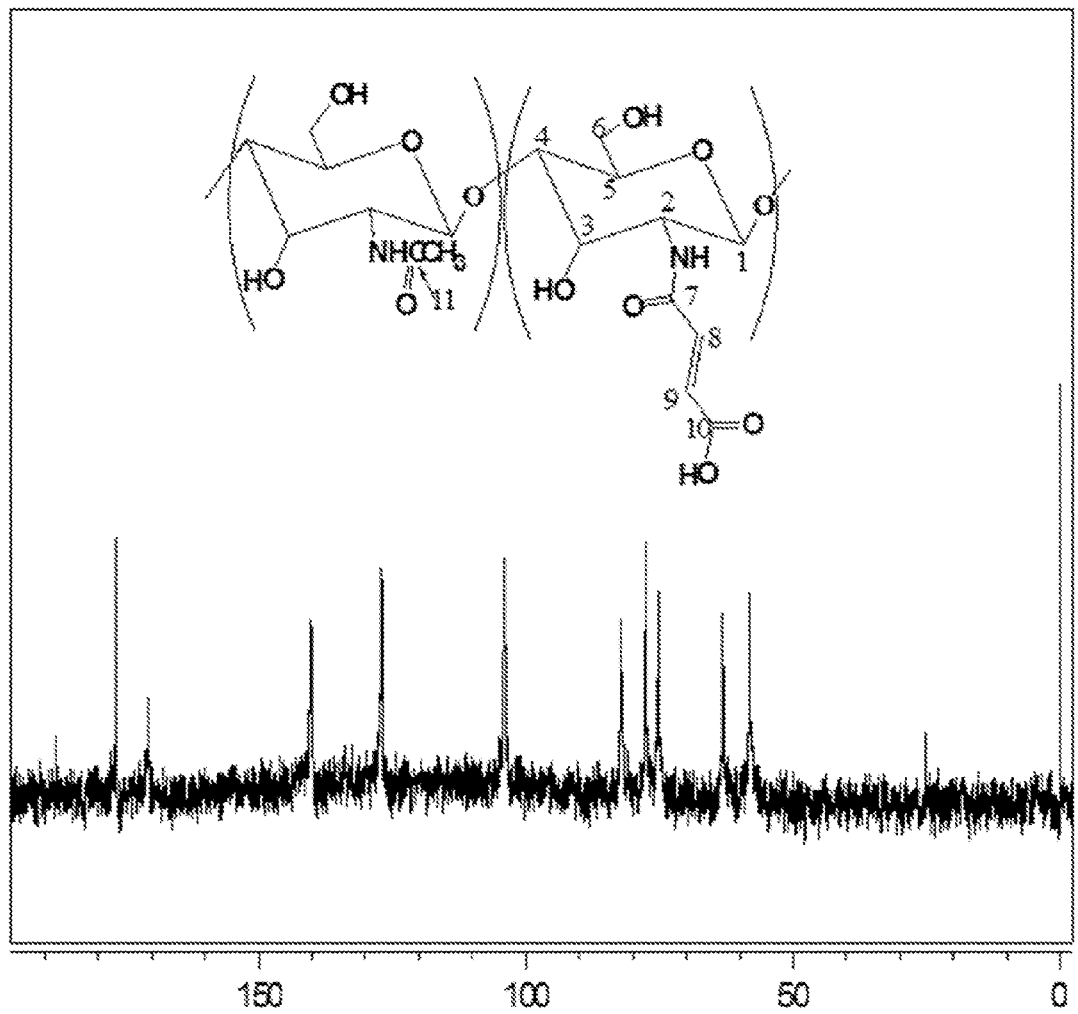

A complete hydrolysis of the ester groups with little influence on the acetyl groups in 0.1M sodium hydroxide solution results in N-maleic chitosan. $^1H$ and $^{13}C$ NMR spectra all indicate the complete removal of substituent groups at hydroxyl group sites, while the substituent at C-2 amino groups almost suffer no adverse effect under the same conditions (FIG. 2a, b). The disappearance of the bands of ester groups at around 1730 $cm^{-1}$ in the IR spectrum of N-maleic Chitosan further confirmed the complete removal of the substituent groups at the two C-6 and C-3 hydroxyl sites. Hence, regioseletive modifications of chitosan at C-2 amino groups is shown.

Figure 2C:
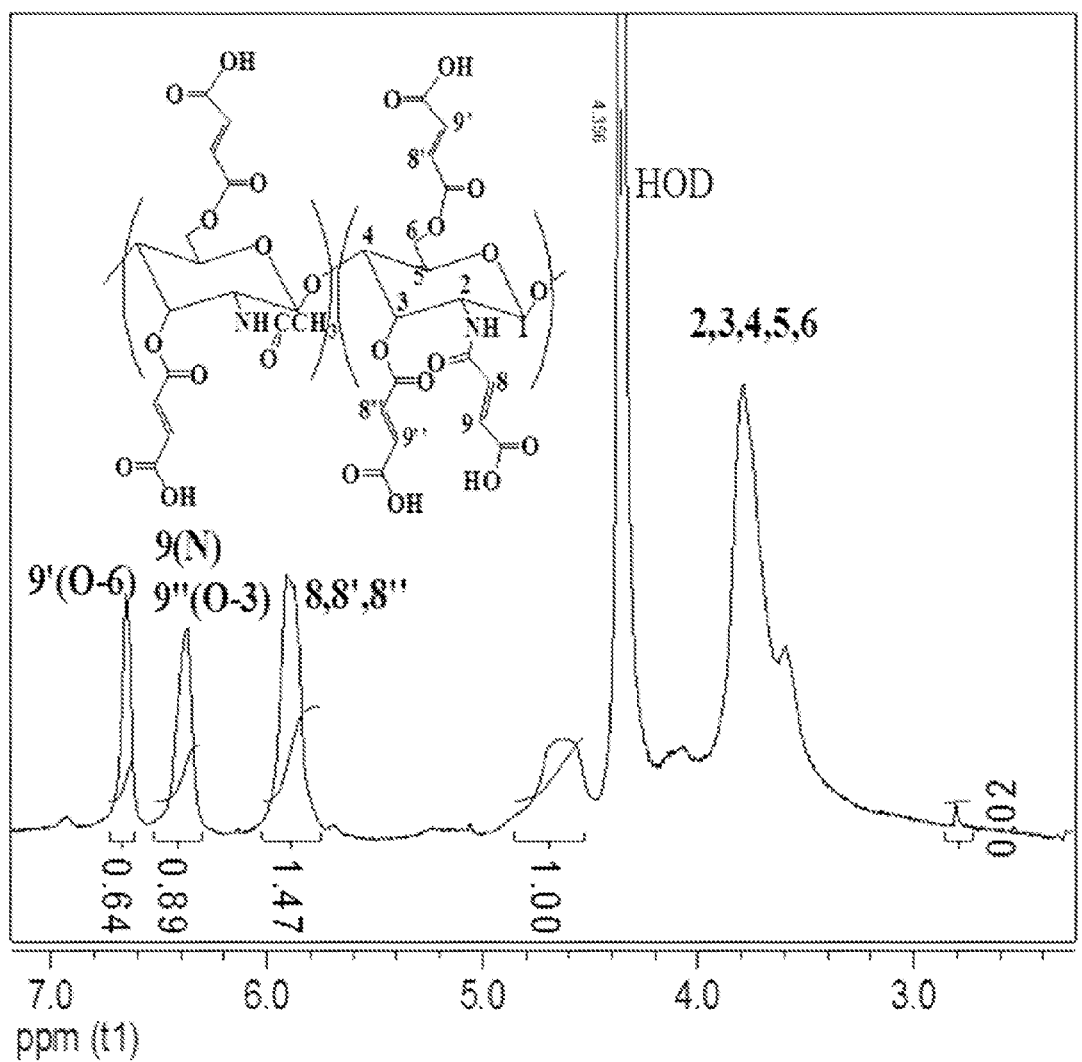
Figure 2D:
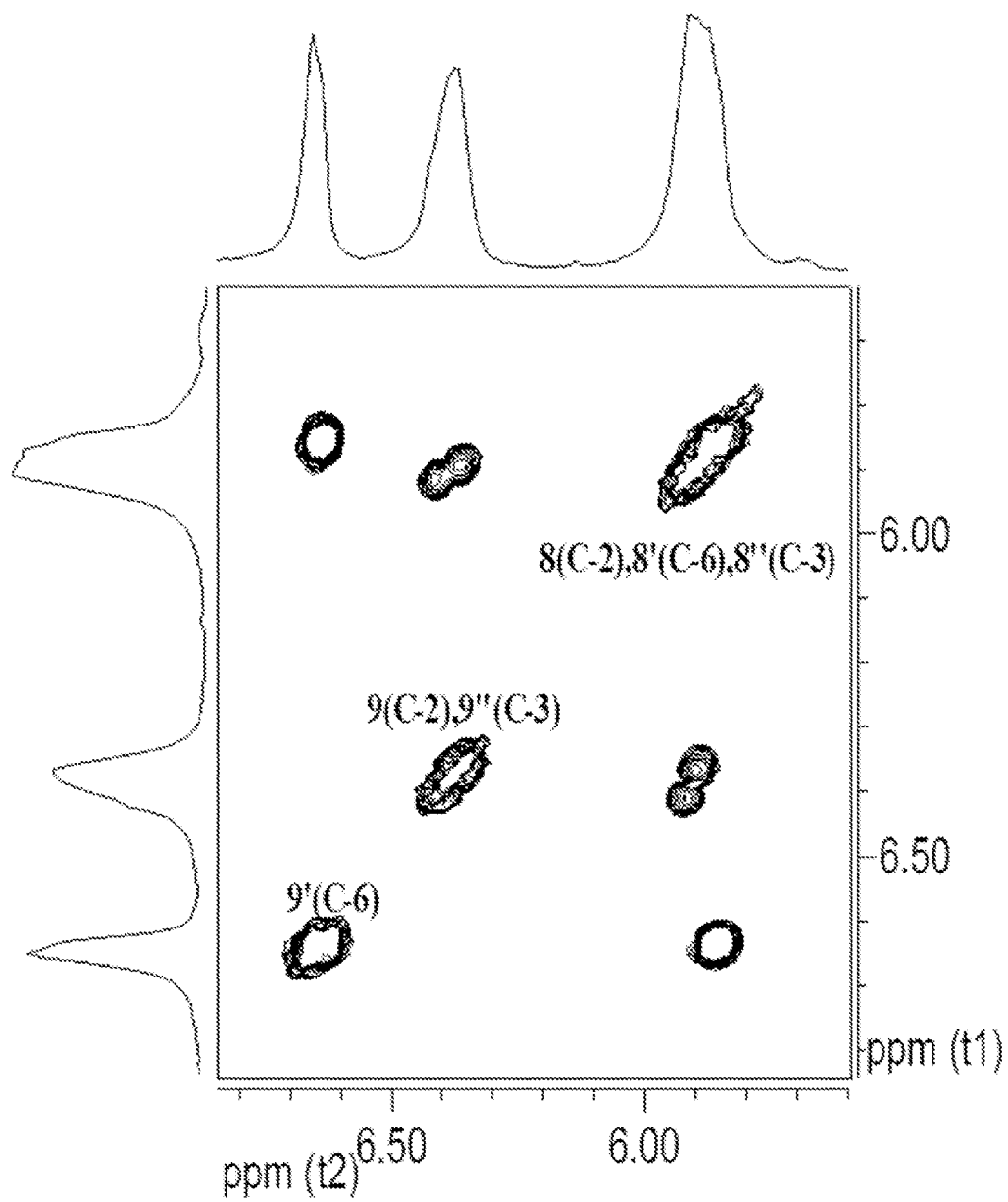
Figure 2E:
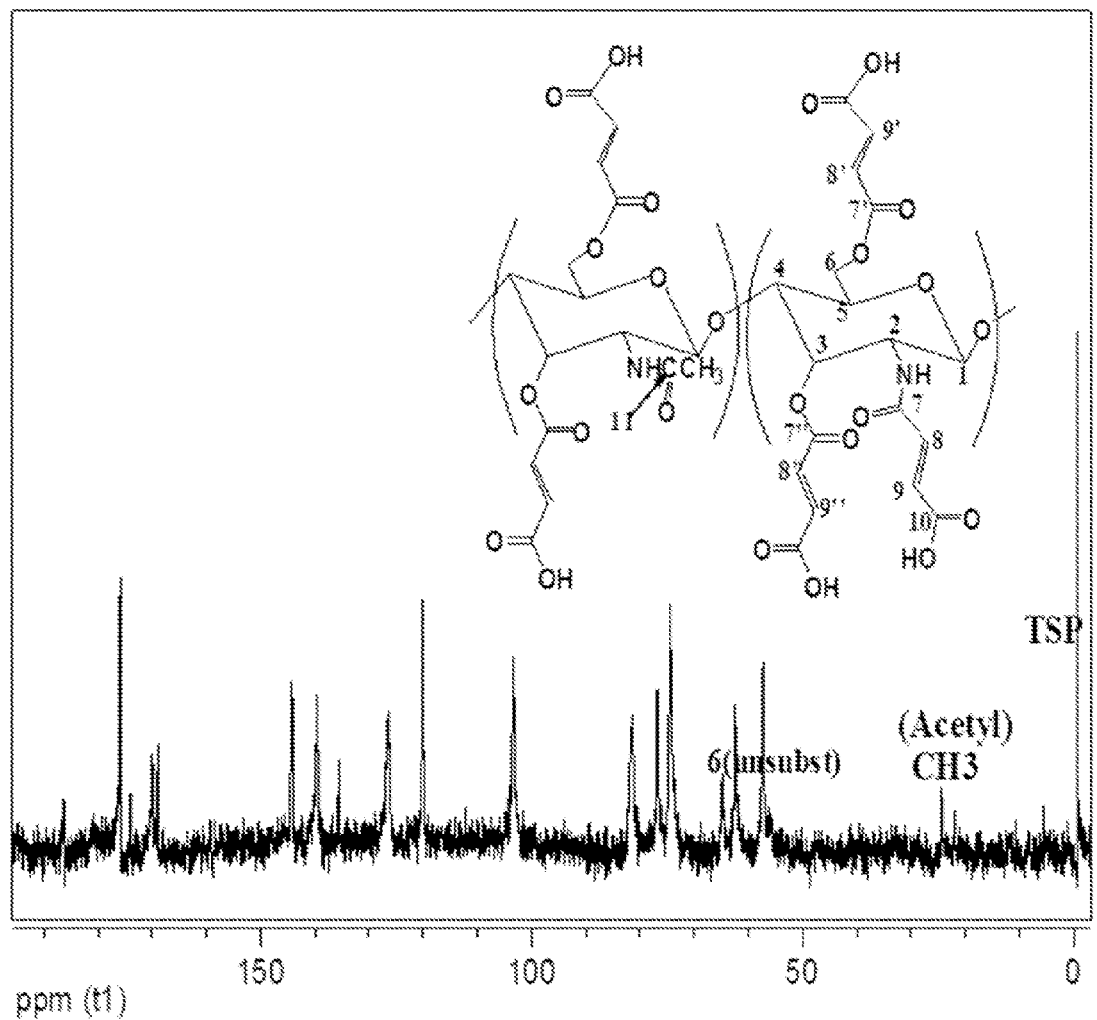

Under the homogeneous reaction conditions, substitutions took place at both amino groups and hydroxyl groups of chitosan, as indicated by the multiple signals from the double bond structure in the $^1H$, $^{13}C$ NMR (FIG. 2c, d). $^1H$-$^1H$ COSY NMR further confirmed that substitutions not only occurred at the C-6 hydroxyl groups and C-2 amino groups, but also the relatively less active C-3 hydroxyl groups, as 3 different signals off the diagonal appear in the region of double bond signals in $^1H$-$^1H$ COSY NMR (FIG. 2e).

The 3 different signals directly come from the couplings between neighboring protons of the double bond structure in 3 different molecular environments, or more specifically, different substituent positions. Among the three substitution sites on chitosan unit, the substitutions took place mainly at C-2 amine site, followed by C-6 hydroxyl group site, whereas the least substitution occurred at C-3 hydroxyl group site. This suggests that an ionic linkage exits between ionized amine and methanesulfonic anions, and that the substitution still successfully takes place at the C-2 amino groups. This is probably due to the easy cleavage of relatively weak ionic links between methanesulfonic or tolunesulfonic anions and ionized amines. The complete removal of the anions was confirmed both in FT-IR (FIG. 1) and NMR (FIG. 2c, e) spectra, as all the signals from the anions were gone in the spectra of the final products.

EXAMPLE 9

N,O-Maleic chitosan (degree of substitution, DS=1.3) and PEGDA are combined in an aqueous solution. A photoinitiator (i.e., Irgacure 2959) at an concentration of 0.5% is added. The solution is subjected to UV light to form a maleic chitosan-PEGDA hydrogel having weight ratio of PEGDA to Maleic chitosan of 2:1, and wherein the PEGDA has a molecular weight of approximately 700 D.

Figure 3:
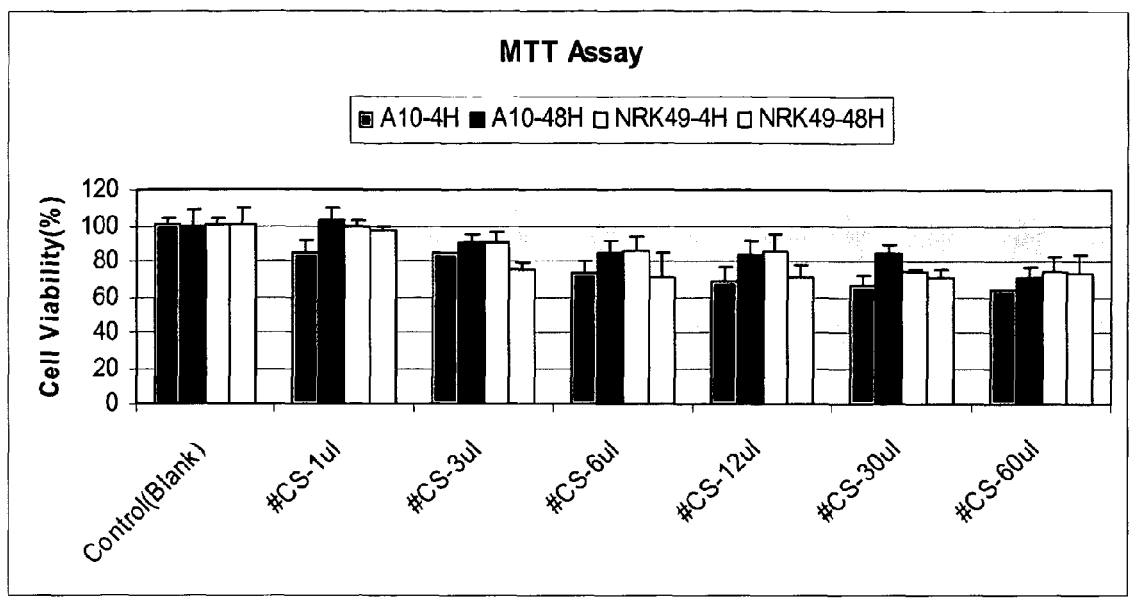
FIG. 3 shows the results of an MTT assay.
Figure 4:
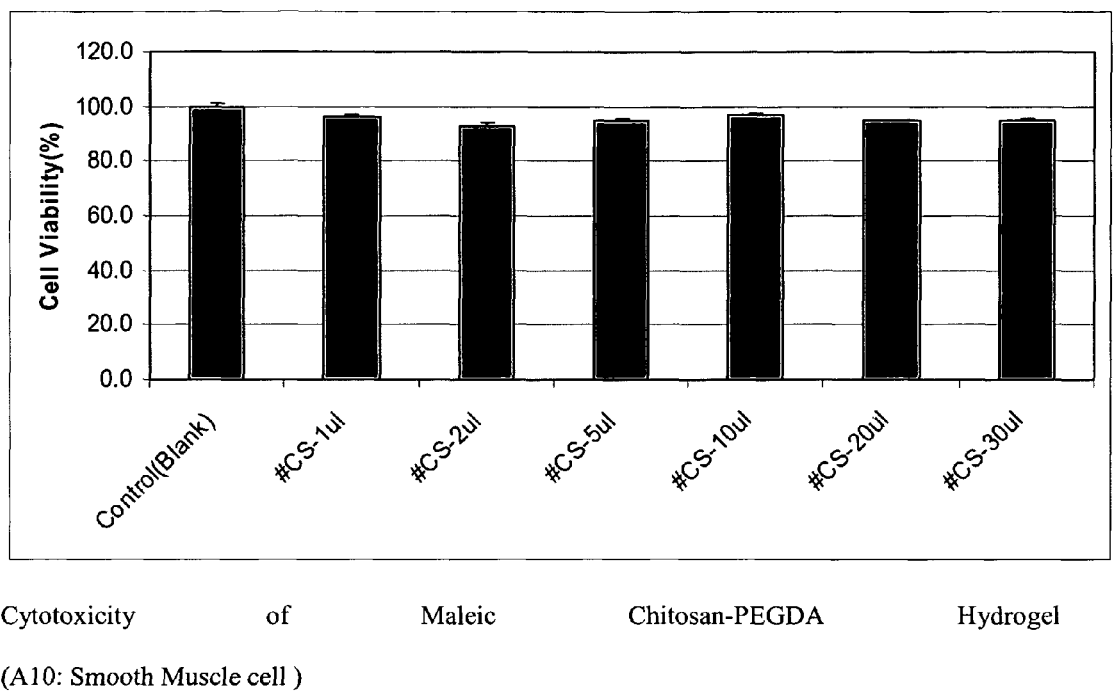
FIG. 4 displays the results of an experiment studying the cytotoxicity of maleic chitosan-PEGDA hydrogel on smooth muscle cell.
Figure 5:
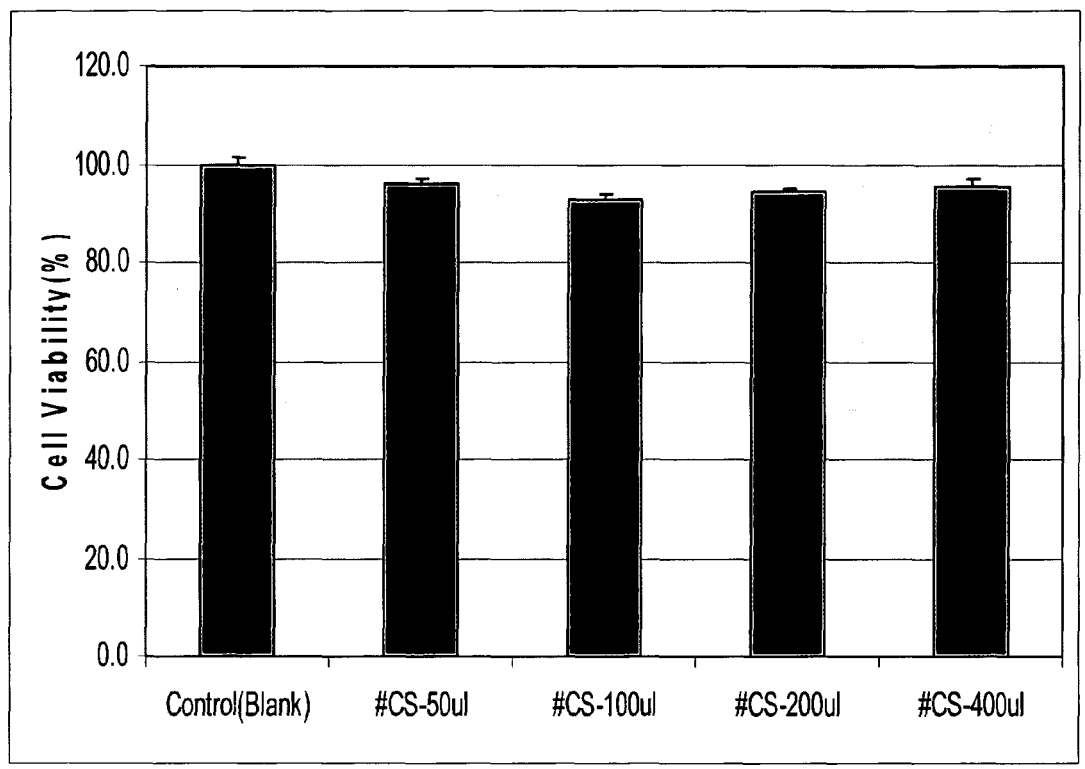
FIG. 5 shows the results of an experiment studying the cytotoxicity of maleic chitosan-PEGDA hydrogel on rat smooth muscle primary cell.

An Microculture Tetrazolium Assay (MTA) Assay is undertaken with A10 smooth muscle cell and NRK49 fibroblast cells. The results of the MTA assay are shown in FIG. 3. Cytotoxicity were of N,O-maleic chitosan on A10 smooth muscle Cell and Rat Smooth Muscle Primary Cell were used in the cytotoxicity test of gel sample. For cytotoxicity tests, 1 wt % maleic chitosan solution was added into the cell media (96 well). After incubation for 4 hours and 48 hours, the cytotoxicity of maleic chitosan was tested. (A10: smooth Muscle cell, NRK49: Fibroblast Cell were used). Maleic chitosan-PEGDA hydrogel (50 mg) was swelled in 10 ml distilled water (weight of swollen gel 2.0 g around) and stored at room temperature for 10 days. Then the solution was taken out and added into the media (96 well). After incubation for 48 hours, the cytotoxicity of hydrogel was tested. (A10: smooth muscle Cell and Rat Smooth Muscle Primary Cell were used). The results are shown in FIGS. 4 and 5.

EXAMPLE 10

Approximately 0.2130 grams of $AgNO_3$ were measured out and dissolved in 9.96 millimeters of DI water in a glass beaker. One unit sample of Maleic chitosan, weighing about 5 mg was immersed in the silver nitrate solution for approximately 6 to 54 hours allow for silver to replace the sodium ions within the hydrogel. The resulting hydrogel was then rinsed using DI water and prepared for SEM/EDS and Electron Microprobe analysis. The membranes that are produced can be characterized as follows:

TABLE 2

| Chitosan Derivative | Soak time length in $AgNO_3$ |
| --- | --- |
| Maleic Chitosan/PEGDA gel (PEG MW 8000) | Soak time 6 hrs |
| | Soak time 24 hrs |
| | Soak time 48 hrs |
| | Soak time 54 hrs |

Bacterial isolates were suspended in sterile saline so that the visual turbidity was equivalent to a 0.5 McFarland standard. This bacterial suspension was used directly for the disk diffusion test. In Rotterdam, the inoculum was prepared by suspending bacteria in 0.45% sterile saline to the equivalent of a 0.5 McFarland turbidity standard using a photometric device. Four microorganisms were tested: *S. Aureus*, *Kleb E. Coli*, and *P. Aerug*.

The disk diffusion method was performed as recommended by the CLSI (National Committee for Clinical Laboratory Standards, 2000a,b,c). Briefly, the bacterial suspension was spread on the surface of a Mueller-Hinton agar. After overnight incubation at 35° C. in air, inhibition zones were measured with a ruler or caliper and the zones were recorded in millimeter.

Antimicrobial testing was performed by taking silver nitrate soaked maleic chitosan/PEGDA gel samples and plating them on an agar plate embedded with each of the 4 bacteria. The antimicrobial property was determined by the clear zone around the maleic chitosan/PEGDA gels. The size of the clear zone around the gel samples were measured and visually recorded. The results are as follows:

TABLE 3

| Compound | S. Aureus | Kleb | E. Coli | P. Aerug |
| --- | --- | --- | --- | --- |
| Maleic chitosan/ PEGDA gels with 6 hrs in $AgNO_3$ | Good efficacy | No effect | Good efficacy | No effect |
| Maleic chitosan/ PEGDA gels with 24 hrs in $AgNO_3$ | Good efficacy | No effect | Good efficacy | No effect |
| Maleic chitosan/ PEGDA gels with 48 hrs in $AgNO_3$ | Good efficacy | No effect | Good efficacy | No effect |
| Maleic chitosan/ PEGDA gels with 54 hrs in $AgNO_3$ | Good efficacy | No effect | Good efficacy | No effect |

EXAMPLE 11

Chitosan Derivative (Polyglutamic Acid Hybrid)

An z-benzyl-glutamic acid is dispersed in tetrahydrafuran at 45° C. for 3 hours to obtain Z-benzyl-glutamic acid NCA. Z-benzyl-glutamic acid NCA is dispersed in DMSO at room temperature for four days with chitosan methanesulfonate or chitosan toluenesulfonate at room temperature for four days to obtain a chitosan derivative with Z-benzyl-glutamic acid NCA attached. The chitosan derivative with Z-benzyl-glutamic acid NCA is deprotected with a reaction utilizing 1N NaOH at room temperature for 12 hours. The reaction is as follows:

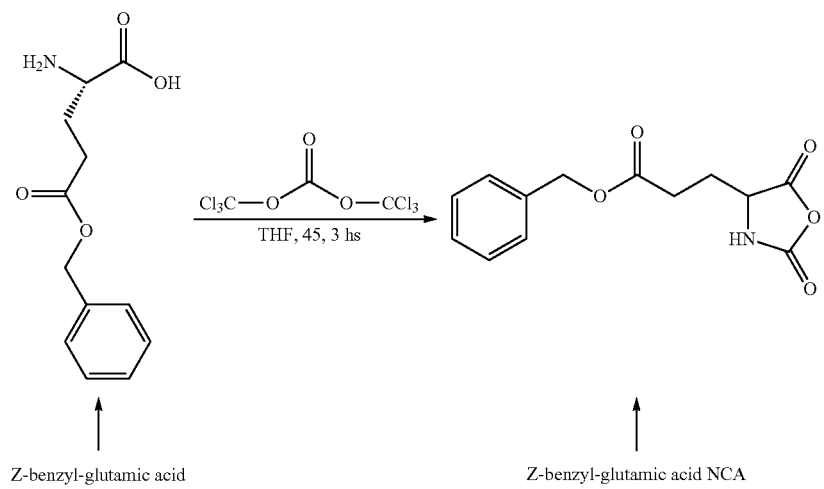

Z-benzyl-glutamic acid          Z-benzyl-glutamic acid NCA

-continued

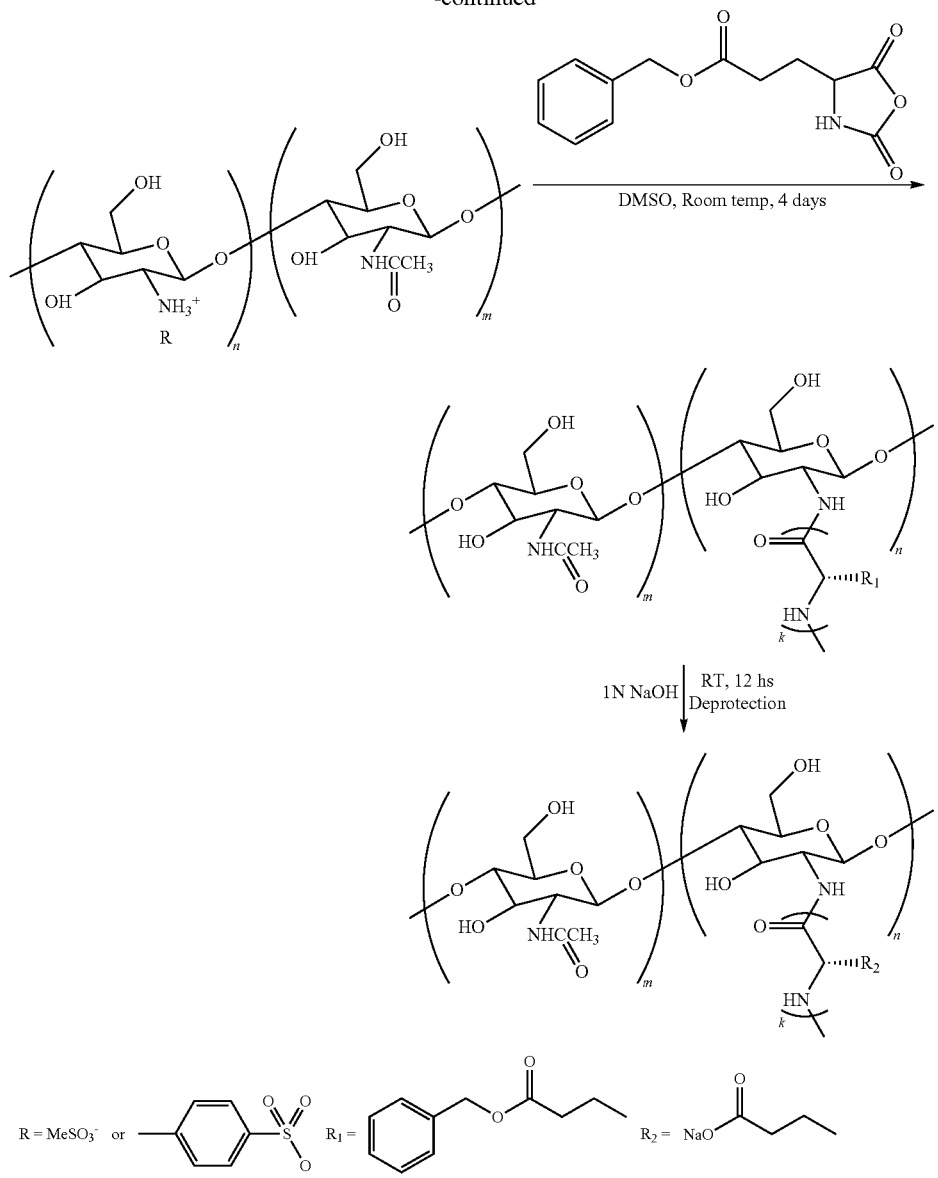

Figure 6:
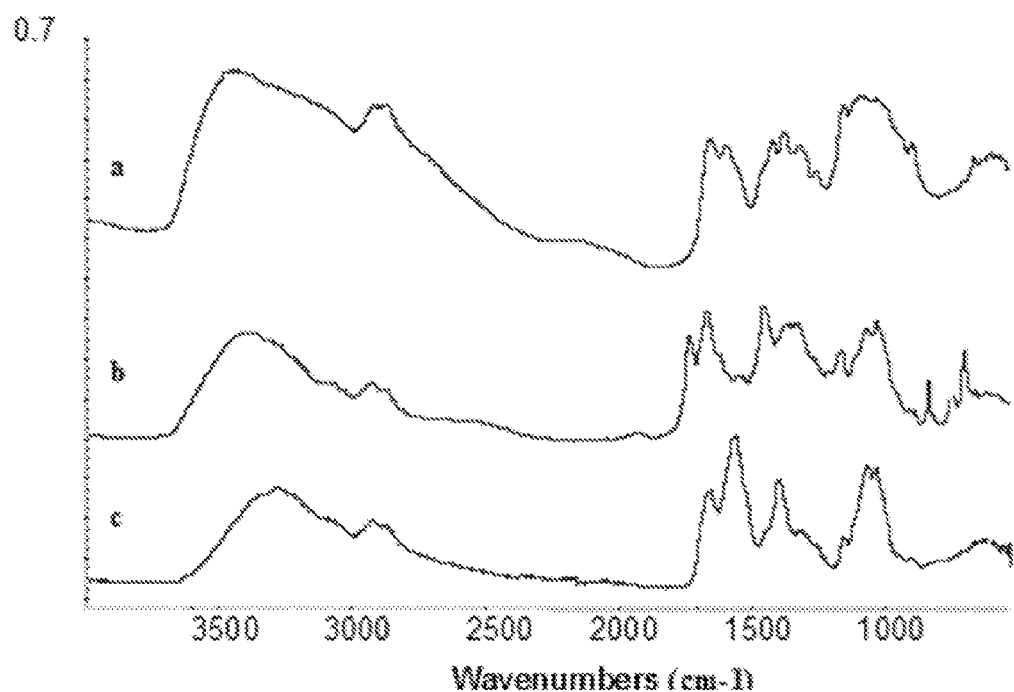
FIG. 6 shows an FTIR of a) chitosan, b) poly-benzyl-glutamate chitosan, and c) polyglutamic acid chitosan.
Figure 7:
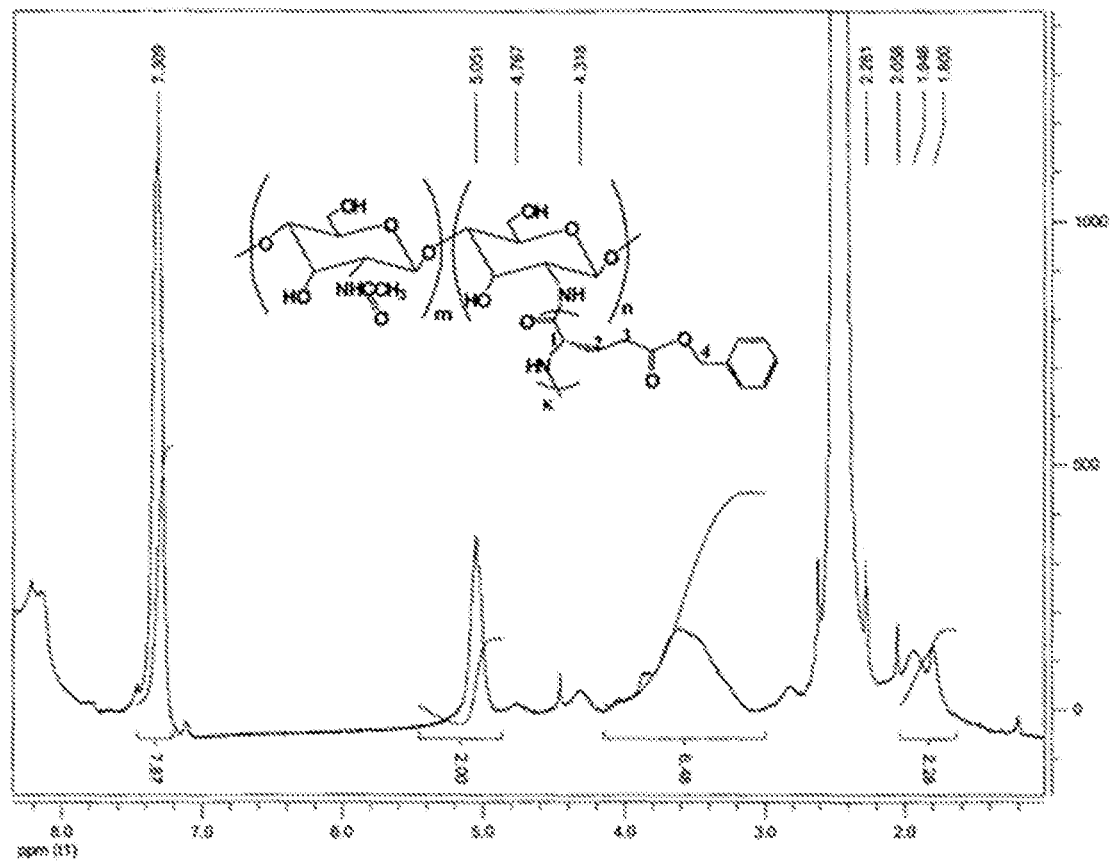
FIG. 7 shows an NMR of Chitosan/poly (Z-benzyl-glutamic acid).
Figure 8:
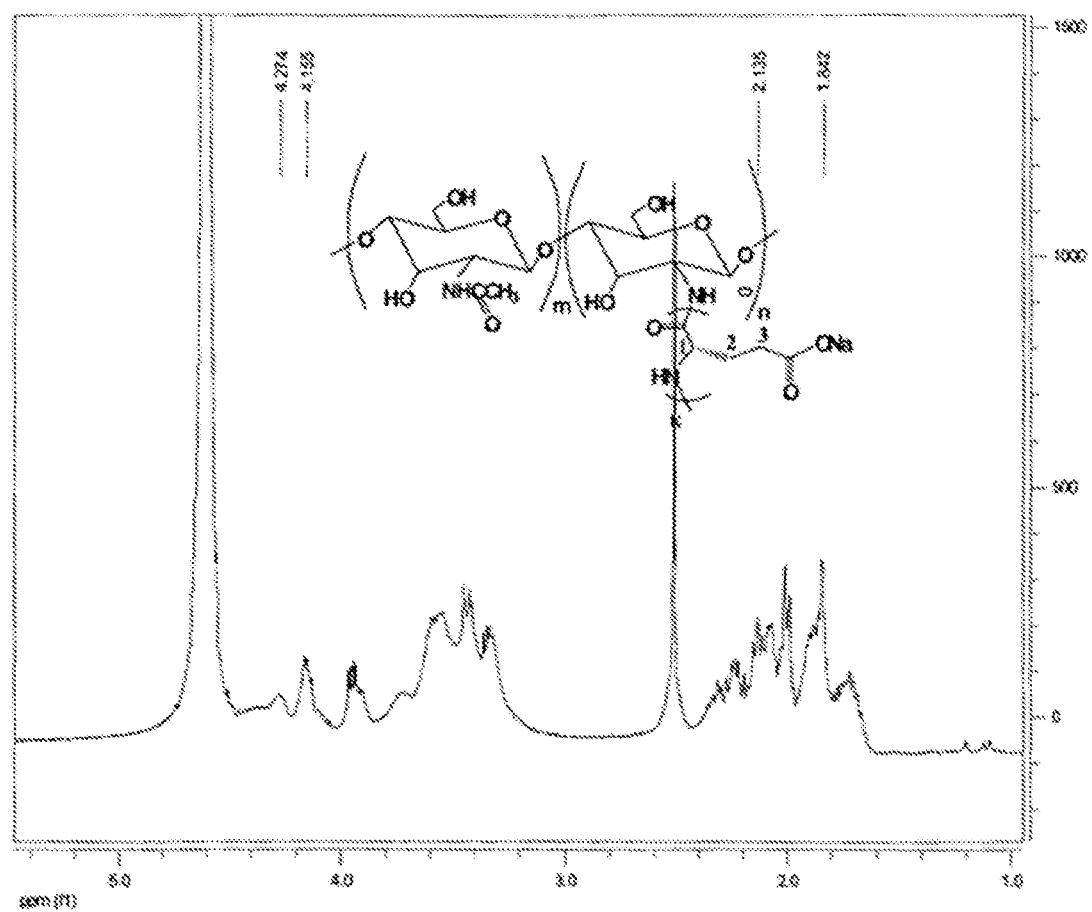
FIG. 8 shows an NMR of chitosan poly-(glutamic acid).

The resulting poly-benzyl glutamate chitosan is analyzed with FTIR (see FIG. 6) and NMR (see FIG. 7).

EXAMPLE 12

Chitosan Derivative—Chitosan Polyleucine Hybrid
(No Need for Deprotection)

Leucine is dispersed in tetrahydrafuran and 45° C. for 3 hours to obtain leucine NCA. Leucine NCA is dispersed in DMSO at room temperature with chitosan methanesulfonate or chitosan toluenesulfonate at room temperature to obtain a chitosan derivative with leucine attached (i.e., Chitosan-Polyleucine). A deprotection step is not required. The reaction is as follows:

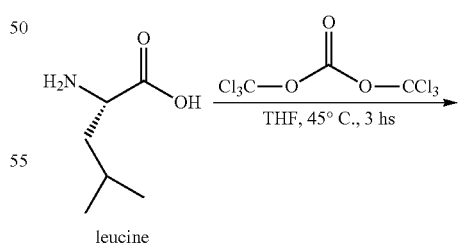
leucine

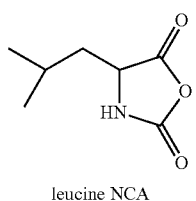
leucine NCA

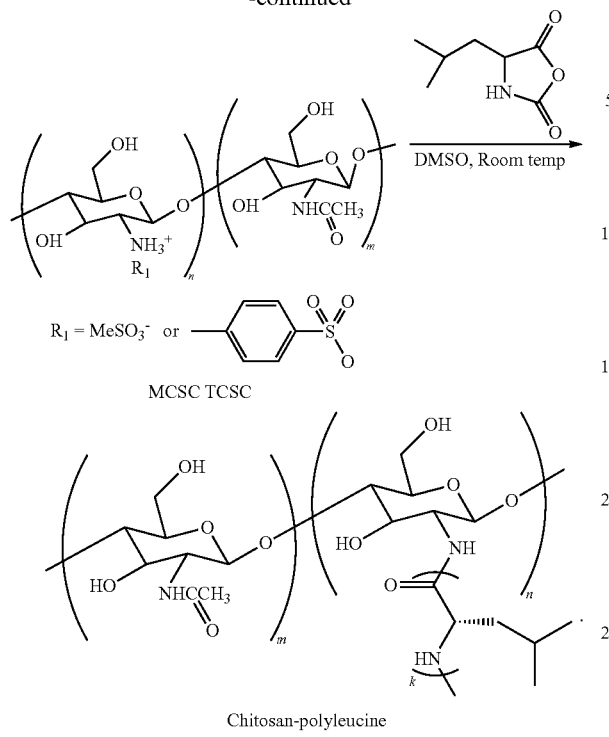

MCSC TCSC

Chitosan-polyleucine

What is claimed:

1. A method for preparing chitosan derivative, comprising:
   i) dispersing chitosan in an aqueous solution to form a first mixture;
   ii) adding a chitosan salt forming acid to the first mixture;
   iii) stirring the first mixture containing the chitosan salt forming acid to form a homogenous solution;
   iv) adding a solvent to the homogenous solution to precipitate an organo-soluble chitosan salt, wherein the organo-soluble chitosan salt is selected from the group consisting of chitosan sulfonate, chitosan methanesulfonate, chitosan toluenesulfonate, chitosan camphorsulfonate, chitosan salicylate, chitosan trifluoromethanesulfonate, chitosan ethanesulfonate, chitosan phenylbenzimidazolesulfonate, chitosan 1-propanesulfonate, (1R)-(−)-10-camphorsulfonate, and chitosan camphorquinone-10-sulfonate;
   v) recovering the organo-soluble chitosan salt;
   vi) dissolving the organo-soluble chitosan salt in formamide to form a second mixture;
   vii) adding a chitosan derivative forming compound to the second mixture;
   viii) reacting the chitosan derivative forming compound with the organo-soluble chitosan salt to obtain a reaction solution containing the chitosan derivative;
   ix) stopping the reaction;
   x) adding a second solvent to the reaction solution to precipitate the chitosan derivative; and
   xi) recovering the chitosan derivative.

2. The method according to claim 1, wherein the organo-soluble chitosan salt is chitosan methanesulfonate, or chitosan toluenesulfonate.

3. The method according to claim 1, wherein the chitosan derivative forming compound is N-carboxy α-amino acid anhydrides (NCA) or cyclic anhydride.

4. The method according to claim 1, further comprising dialyzing the recovered chitosan derivative and freeze-drying the dialyzed chitosan derivative.

5. The method according to claim 1, wherein the second solvent is acetone or isopropanol.

* * * * *